(12) United States Patent
Boyd et al.

(10) Patent No.: US 7,655,426 B2
(45) Date of Patent: Feb. 2, 2010

(54) EPHRIN-B RECEPTOR PROTEIN INVOLVED IN CARCINOMA

(75) Inventors: Robert Simon Boyd, Abingdon (GB); Graham Charles Fletcher, Abingdon (GB); Lindsey Jane Hudson, Abingdon (GB); Sonal Patel, Abingdon (GB); Jonathan Alexander Terrett, Abingdon (GB)

(73) Assignee: Oxford Glycosciences (UK) Ltd, Abingdon, Oxfordshire (GB)

( * ) Notice: Subject to any disclaimer, the term of this patent is extended or adjusted under 35 U.S.C. 154(b) by 152 days.

(21) Appl. No.: 10/510,524

(22) PCT Filed: Apr. 9, 2003

(86) PCT No.: PCT/GB03/01593

§ 371 (c)(1), (2), (4) Date: Apr. 27, 2005

(87) PCT Pub. No.: WO03/087841

PCT Pub. Date: Oct. 23, 2003

(65) Prior Publication Data

US 2005/0260209 A1 Nov. 24, 2005

(30) Foreign Application Priority Data

Apr. 9, 2002 (GB) ................................. 0208089.3

(51) Int. Cl.
*G01N 33/574* (2006.01)
(52) U.S. Cl. ...................................... 435/7.23; 435/7.1
(58) Field of Classification Search .................. 435/7.1
See application file for complete search history.

(56) References Cited

U.S. PATENT DOCUMENTS 5,981,246 A 11/1999 Fox et al.
2003/0170865 A1* 9/2003 Tajima et al. ............... 435/226

FOREIGN PATENT DOCUMENTS

DE 4233782 4/1994
DE 4233782 A1 * 4/1994
EP 0 659 883 B1 4/2003
WO WO 95/15375 6/1995
WO WO 01/57188 8/2001
WO WO 01/72833 A2 10/2001
WO WO 01/72833 A3 10/2001
WO WO 02/10359 A1 2/2002
WO WO 02/21996 A2 3/2002
WO WO 02/21996 A3 3/2002
WO WO 03/004529 1/2003
WO WO2006/119510 * 11/2006

OTHER PUBLICATIONS

Bowie et al (Science, 1990, 247:1306-1310).*
Tockman et al (Cancer Res., 1992, 52:2711s-2718s).*
Slamon et al. (Science vol. 235, Jan. 1987, pp. 177-182).*
Hock et al (Oncogene, 1998, 17:255-260).*
iHOP, "EPHB3", p. 1.*
NCBI Sequence Viewer for EPHB3, NP_004434, p. 1-5.*
Bohme et al (Oncogene, 1993, 8:2857-2862).*
Hock et al, Oncogene, 1998, 17:255-260.*
Liu et al (Cancer, Feb. 2002, 94:934-939).*
iHOP, "EPHB3", p. 1, 2004.*
Bohme et al (Oncogene, 1993, 8:2857-2862), 2006.*
Kitahara et al (Cancer Research, May 2001, 61:3544-3549).*
Chaib,H, et al., Profiling and Verification of Gene Expression Patterns in Normal and Malignant Human Prostate Tissues by cDNA Microarray Analysis[1], 2001, Neoplasia 3: pp. 43-52.
Tang, XX, et al, Coexpression of Transcripts Encoding EPHB Receptor Protein Tyrosine Kinases and Their Ephrin-B Ligands in Human Small Cell Lung Carcinoma[1], 1999, Clin Cancer Res. Feb;5(2): pp. 455-460.
Hock, B, et al., PDS-domain-mediated interaction of the Eph-related receptor tyrosine kinase EphB3 and the ras-binding protein AF6 depends on the kinase activity of the receptor, 1998, Proc. Natl. Acad. Sci. USA 95: pp. 9779-9784.
Liu, W., et al., Coexpression of Ephrin-Bs and their Receptors in Colon Carcinoma, 2002, Cancer 94: pp. 934-939.
Kitahara, et al., Cancer Research 61, pp. 3544-3549 (2001).

* cited by examiner

*Primary Examiner*—Laura B Goddard
(74) *Attorney, Agent, or Firm*—Klauber & Jackson, LLC

(57) ABSTRACT

The present invention provides a polypeptide (CCMP-1) of use in the diagnosis, screening, treatment and prophylaxis of carcinoma. Also provided are compositions comprising the protein, vaccines and antibodies that are immunospecific for the protein.

6 Claims, 5 Drawing Sheets

WO 03/087841

```
ggctcggctcctagagctgccacggccatggccagagcccgcccgccgccgccgccgtcg 60
                        M   A   R   A   R   P   P   P   P   P   S ccgccgccggggcttctgccgctgctccctccgctgctgctgctgccgctgctgctgctg 120
 P   P   P   G   L   L   P   L   L   P   L   L   L   L   P   L   L   L   L cccgccggctgccgggcgctggaagagaccctcatggacacaaaatgggtaacatctgag 180
 P   A   G   C   R   A   L   E   E   T   L   M   D   T   K   W   V   T   S   E ttggcgtggacatctcatccagaaagtgggtgggaagaggtgagtggctacgatgaggcc 240
 L   A   W   T   S   H   P   E   S   G   W   E   V   S   G   Y   D   E   A atgaatcccatccgcacataccaggtgtgtaatgtgcgcgagtcaagccagaacaactgg 300
 M   N   P   I   R   T   Y   Q   V   C   N   V   R   E   S   S   Q   N   N   W cttcgcacggggttcatctggcggcgggatgtgcagcgggtctacgtggagctcaagttc 360
 L   R   T   G   F   I   W   R   R   D   V   Q   R   V   Y   V   E   L   K   F actgtgcgtgactgcaacagcatccccaacatccccggctcctgcaaggagaccttcaac 420
 T   V   R   D   C   N   S   I   P   N   I   P   G   S   C   K   E   T   F   N ctcttctactacgaggctgacagcgatgtggcctcagcctcctccccttctggatggag 480
 L   F   Y   Y   E   A   D   S   D   V   A   S   A   S   S   P   F   W   M   E aaccctacgtgaaagtggacaccattgcacccgatgagagcttctcgcggctggatgcc 540
 N   P   Y   V   K   V   D   T   I   A   P   D   E   S   F   S   R   L   D   A ggccgtgtcaacaccaaggtgcgcagctttgggccactttccaaggctggcttctacctg 600
 G   R   V   N   T   K   V   R   S   F   G   P   L   S   K   A   G   F   Y   L gccttccaggaccagggcgcctgcatgtcgctcatctccgtgcgcgccttctacaagaag 660
 A   F   Q   D   Q   G   A   C   M   S   L   I   S   V   R   A   F   Y   K   K tgtgcatccaccaccgcaggcttcgcactcttccccgagaccctcactggggcggagccc 720
 C   A   S   T   T   A   G   F   A   L   F   P   E   T   L   T   G   A   E   P acctcgctggtcattgctcctggcacctgcatccctaacgccgtggaggtgtcggtgcca 780
 T   S   L   V   I   A   P   G   T   C   I   P   N   A   V   E   V   S   V   P ctcaagctctactgcaacggcgatggggagtggatggtgcctgtgggtgcctgcacctgt 840
 L   K   L   Y   C   N   G   D   G   E   W   M   V   P   V   G   A   C   T   C gccaccggccatgagccagctgccaaggagtcccagtgccgcccctgtcccctggggagc 900
 A   T   G   H   E   P   A   A   K   E   S   Q   C   R   P   C   P   P   G   S tacaaggcgaagcagggagaggggccctgcctcccatgtcccccaacagccgtaccacc 960
 Y   K   A   K   Q   G   E   G   P   C   L   P   C   P   P   N   S   R   T   T tccccagccgccagcatctgcacctgccacaataacttctaccgtgcagactcggactct 1020
 S   P   A   A   S   I   C   T   C   H   N   N   F   Y   R   A   D   S   D   S gcggacagtgcctgtaccaccgtgccatctccaccccgaggtgtgatctccaatgtgaat 1080
 A   D   S   A   C   T   T   V   P   S   P   P   R   G   V   I   S   N   V   N gaaacctcactgatcctcgagtggagtgagccccgggacctgggtgtccgggatgacctc 1140
 E   T   S   L   I   L   E   W   S   E   P   R   D   L   G   V   R   D   D   L ctgtacaatgtcatctgcaagaagtgccatggggctggaggggcctcagcctgctcacgc 1200
```

Figure 1

```
                L  Y  N  V  I  C  K  K  C  H  G  A  G  G  A  S  A  C  S  R
tgtgatgacaacgtggagtttgtgcctcggcagctgggcctgtcggagccccgggtccac 1260
 C  D  D  N  V  E  F  V  P  R  Q  L  G  L  S  E  P  R  V  H accagccatctgctggcccacacgcgctacacctttgaggtgcaggcggtcaacggtgtc 1320
 T  S  H  L  L  A  H  T  R  Y  T  F  E  V  Q  A  V  N  G  V tcgggcaagagccctctgccgcctcgttatgcggccgtgaatatcaccacaaaccaggct 1380
 S  G  K  S  P  L  P  P  R  Y  A  A  V  N  I  T  T  N  Q  A gccccgtctgaagtgcccacactacgcctgcacagcagctcaggcagcagcctcaccta 1440
 A  P  S  E  V  P  T  L  R  L  H  S  S  G  S  S  L  T  L tcctgggcaccccagagcggcccaacggagtcatcctggactacgagatgaagtacttt 1500
 S  W  A  P  P  E  R  P  N  G  V  I  L  D  Y  E  M  K  Y  F gagaagagcgagggcatcgcctccacagtgaccagccagatgaactccgtgcagctggac 1560
 E  K  S  E  G  I  A  S  T  V  T  S  Q  M  N  S  V  Q  L  D gggcttcggcctgacgcccgctatgtggtccaggtccgtgcccgcacagtagctggctat 1620
 G  L  R  P  D  A  R  Y  V  V  Q  V  R  A  R  T  V  A  G  Y gggcagtacagccgccctgccgagtttgagaccacaagtgagagaggctctggggcccag 1680
 G  Q  Y  S  R  P  A  E  F  E  T  T  S  E  R  G  S  G  A  Q cagctccaggagcagcttcccctcatcgtgggctccgctacagctgggcttgtcttcgtg 1740
 Q  L  Q  E  Q  L  P  L  I  V  G  S  A  T  A  G  L  V  F  V gtggctgtcgtggtcatcgctatcgtctgcctcaggaagcagcgacacggctctgattcg 1800
 V  A  V  V  V  I  A  I  V  C  L  R  K  Q  R  H  G  S  D  S gagtacacggagaagctgcagcagtacattgctcctggaatgaaggtttatattgaccct 1860
 E  Y  T  E  K  L  Q  Q  Y  I  A  P  G  M  K  V  Y  I  D  P tttacctacgaggaccctaatgaggctgttcgggagtttgccaaggagatcgacgtgtcc 1920
 F  T  Y  E  D  P  N  E  A  V  R  E  F  A  K  E  I  D  V  S tgcgtcaagatcgaggaggtgatcggagctggggaatttggggaagtgtgccgtggtcga 1980
 C  V  K  I  E  E  V  I  G  A  G  E  F  G  E  V  C  R  G  R ctgaaacagcctggccgccgagaggtgtttgtggccatcaagacgctgaaggtgggctac 2040
 L  K  Q  P  G  R  R  E  V  F  V  A  I  K  T  L  K  V  G  Y accgagaggcagcggcgggacttcctaagcgaggcctccatcatgggtcagtttgatcac 2100
 T  E  R  Q  R  R  D  F  L  S  E  A  S  I  M  G  Q  F  D  H cccaatataatccggctcgagggcgtggtcaccaaaagtcggccagttatgatcctcact 2160
 P  N  I  I  R  L  E  G  V  V  T  K  S  R  P  V  M  I  L  T gagttcatggaaaactgcgccctggactccttcctccggctcaacgatgggcagttcacg 2220
 E  F  M  E  N  C  A  L  D  S  F  L  R  L  N  D  G  Q  F  T gtcatccagctggtgggcatgttgcggggcattgctgccggcatgaagtacctgtccgag 2280
 V  I  Q  L  V  G  M  L  R  G  I  A  A  G  M  K  Y  L  S  E atgaactatgtgcaccgcgacctggctgctcgcaacatccttgtcaacagcaacctggtc 2340
 M  N  Y  V  H  R  D  L  A  A  R  N  I  L  V  N  S  N  L  V
```

Figure 1 continued

```
tgcaaagtctcagactttggcctctcccgcttcctggaggatgacccctccgatcctacc 2400
 C   K   V   S   D   F   G   L   S   R   F   L   E   D   D   P   S   D   P   T tacaccagttccctgggcgggaagatccccatccgctggactgccccagaggccatagcc 2460
 Y   T   S   S   L   G   G   K   I   P   I   R   W   T   A   P   E   A   I   A tatcggaagttcacttctgctagtgatgtctggagctacggaattgtcatgtgggaggtc 2520
 Y   R   K   F   T   S   A   S   D   V   W   S   Y   G   I   V   M   W   E   V atgagctatggagagcgaccctactgggacatgagcaaccaggatgtcatcaatgccgtg 2580
 M   S   Y   G   E   R   P   Y   W   D   M   S   N   Q   D   V   I   N   A   V gagcaggattaccggctgccaccacccatggactgtcccacagcactgcaccagctcatg 2640
 E   Q   D   Y   R   L   P   P   P   M   D   C   P   T   A   L   H   Q   L   M ctggactgctgggtgcgggaccggaacctcaggcccaaattctcccagattgtcaatacc 2700
 L   D   C   W   V   R   D   R   N   L   R   P   K   F   S   Q   I   V   N   T ctggacaagctcatccgcaatgctgccagcctcaaggtcattgccagcgctcagtctggc 2760
 L   D   K   L   I   R   N   A   A   S   L   K   V   I   A   S   A   Q   S   G atgtcacagcccctcctggaccgcacggtcccagattacacaaccttcacgacagttggt 2820
 M   S   Q   P   L   L   D   R   T   V   P   D   Y   T   T   F   T   T   V   G gattggctggatgccatcaagatggggcggtacaaggagagcttcgtcagtgcggggttt 2880
 D   W   L   D   A   I   K   M   G   R   Y   K   E   S   F   V   S   A   G   F gcatcttttgacctggtggcccagatgacggcagaagacctgctccgtattggggtcacc 2940
 A   S   F   D   L   V   A   Q   M   T   A   E   D   L   L   R   I   G   V   T ctggccggccaccagaagaagatcctgagcagtatccaggacatgcggctgcagatgaac 3000
 L   A   G   H   Q   K   K   I   L   S   S   I   Q   D   M   R   L   Q   M   N cagacgctgcctgtgcaggtctgacaccggctcccacggggaccctgaggaccgtgcagg 3060
 Q   T   L   P   V   Q   V   * gatgccaagcagccggctggactttcggactcttggacttttggatgcctggccttaggc 3120
tgtggcccagaagctggaagtttgggaaaggcccaagctgggacttctccaggcctgtgt 3180
tccctccccaggaagtgcgcccaaacctcttcatattgaagatggattaggagaggggg  3240
tgatgacccctccccaagcccctcagggcccagaccttcctgctctccagcaggggatcc 3300
ccacaacctcacacttgtctgttcttcagtgctggaggtcctggcagggtcaggctgggg 3360
taagccggggttccacagggcccagccctggcaggggtctggccccccaggtaggcggag 3420
agcagtccctccctcaggaactggaggaggggactccaggaatggggaaatgtgacacca 3480
ccatcctgaagccagcttgcacctccagtttgcacagggatttgtcctggggctgaggg  3540
ccctgtccccacccccgcccttggtgctgtcataaaagggcaggcaggggcaggctgagg 3600
agttgcccgttgcccccccagagactgactctcagagccagagatgggatgtgtgagtgtg 3660
tgtgtgtgtgtgcgcgcgcgcgcgtgtgtgtgcacgcactggcctgcacagaga        3720
gcatgggtgagcgtgtaaaagcttggccctgtgccctacagtggggacagctgggccgac  3780
agcagaataaaggcaataagatgaa 3805
```

Figure 1 continued

SEQUENCE LISTING

<160> NUMBER OF SEQ ID NOS: 9

<210> SEQ ID NO 1
<211> LENGTH: 998
<212> TYPE: PRT
<213> ORGANISM: Homo sapiens

<400> SEQUENCE: 1

Met Ala Arg Ala Arg Pro Pro Pro Pro Ser Pro Pro Gly Leu
1               5                   10                  15

Leu Pro Leu Leu Pro Pro Leu Leu Leu Leu Pro Leu Leu Leu Pro
                20                  25                  30

Ala Gly Cys Arg Ala Leu Glu Glu Thr Leu Met Asp Thr Lys Trp Val
            35                  40                  45

Thr Ser Glu Leu Ala Trp Thr Ser His Pro Glu Ser Gly Trp Glu Glu
        50                  55                  60

Val Ser Gly Tyr Asp Glu Ala Met Asn Pro Ile Arg Thr Tyr Gln Val
65                  70                  75                  80

Cys Asn Val Arg Glu Ser Ser Gln Asn Asn Trp Leu Arg Thr Gly Phe
                85                  90                  95

Ile Trp Arg Arg Asp Val Gln Arg Val Tyr Val Glu Leu Lys Phe Thr
            100                 105                 110

Val Arg Asp Cys Asn Ser Ile Pro Asn Ile Pro Gly Ser Cys Lys Glu

-continued

```
            115                 120                 125
Thr Phe Asn Leu Phe Tyr Tyr Glu Ala Asp Ser Asp Val Ala Ser Ala
            130                 135                 140
Ser Ser Pro Phe Trp Met Glu Asn Pro Tyr Val Lys Val Asp Thr Ile
145                 150                 155                 160
Ala Pro Asp Glu Ser Phe Ser Arg Leu Asp Ala Gly Arg Val Asn Thr
                165                 170                 175
Lys Val Arg Ser Phe Gly Pro Leu Ser Lys Ala Gly Phe Tyr Leu Ala
            180                 185                 190
Phe Gln Asp Gln Gly Ala Cys Met Ser Leu Ile Ser Val Arg Ala Phe
            195                 200                 205
Tyr Lys Lys Cys Ala Ser Thr Thr Ala Gly Phe Ala Leu Phe Pro Glu
            210                 215                 220
Thr Leu Thr Gly Ala Glu Pro Thr Ser Leu Val Ile Ala Pro Gly Thr
225                 230                 235                 240
Cys Ile Pro Asn Ala Val Glu Val Ser Val Pro Leu Lys Leu Tyr Cys
                245                 250                 255
Asn Gly Asp Gly Glu Trp Met Val Pro Val Gly Ala Cys Thr Cys Ala
                260                 265                 270
Thr Gly His Glu Pro Ala Ala Lys Glu Ser Gln Cys Arg Pro Cys Pro
            275                 280                 285
Pro Gly Ser Tyr Lys Ala Lys Gln Gly Glu Gly Pro Cys Leu Pro Cys
            290                 295                 300
Pro Pro Asn Ser Arg Thr Thr Ser Pro Ala Ala Ser Ile Cys Thr Cys
305                 310                 315                 320
His Asn Asn Phe Tyr Arg Ala Asp Ser Asp Ser Ala Asp Ser Ala Cys
                325                 330                 335
Thr Thr Val Pro Ser Pro Pro Arg Gly Val Ile Ser Asn Val Asn Glu
                340                 345                 350
Thr Ser Leu Ile Leu Glu Trp Ser Glu Pro Arg Asp Leu Gly Val Arg
            355                 360                 365
Asp Asp Leu Leu Tyr Asn Val Ile Cys Lys Lys Cys His Gly Ala Gly
            370                 375                 380
Gly Ala Ser Ala Cys Ser Arg Cys Asp Asp Asn Val Glu Phe Val Pro
385                 390                 395                 400
Arg Gln Leu Gly Leu Ser Glu Pro Arg Val His Thr Ser His Leu Leu
                405                 410                 415
Ala His Thr Arg Tyr Thr Phe Glu Val Gln Ala Val Asn Gly Val Ser
            420                 425                 430
Gly Lys Ser Pro Leu Pro Pro Arg Tyr Ala Ala Val Asn Ile Thr Thr
            435                 440                 445
Asn Gln Ala Ala Pro Ser Glu Val Pro Thr Leu Arg Leu His Ser Ser
            450                 455                 460
Ser Gly Ser Ser Leu Thr Leu Ser Trp Ala Pro Pro Glu Arg Pro Asn
465                 470                 475                 480
Gly Val Ile Leu Asp Tyr Glu Met Lys Tyr Phe Glu Lys Ser Glu Gly
                485                 490                 495
Ile Ala Ser Thr Val Thr Ser Gln Met Asn Ser Val Gln Leu Asp Gly
                500                 505                 510
Leu Arg Pro Asp Ala Arg Tyr Val Val Gln Val Arg Ala Arg Thr Val
            515                 520                 525
Ala Gly Tyr Gly Gln Tyr Ser Arg Pro Ala Glu Phe Glu Thr Thr Ser
            530                 535                 540
```

-continued

```
Glu Arg Gly Ser Gly Ala Gln Gln Leu Gln Glu Gln Leu Pro Leu Ile
545                 550                 555                 560

Val Gly Ser Ala Thr Ala Gly Leu Val Phe Val Ala Val Val
                565                 570                 575

Ile Ala Ile Val Cys Leu Arg Lys Gln Arg His Gly Ser Asp Ser Glu
                580                 585                 590

Tyr Thr Glu Lys Leu Gln Gln Tyr Ile Ala Pro Gly Met Lys Val Tyr
        595                 600                 605

Ile Asp Pro Phe Thr Tyr Glu Asp Pro Asn Glu Ala Val Arg Glu Phe
            610                 615                 620

Ala Lys Glu Ile Asp Val Ser Cys Val Lys Ile Glu Glu Val Ile Gly
625                 630                 635                 640

Ala Gly Glu Phe Gly Glu Val Cys Arg Gly Arg Leu Lys Gln Pro Gly
                645                 650                 655

Arg Arg Glu Val Phe Val Ala Ile Lys Thr Leu Lys Val Gly Tyr Thr
                660                 665                 670

Glu Arg Gln Arg Arg Asp Phe Leu Ser Glu Ala Ser Ile Met Gly Gln
        675                 680                 685

Phe Asp His Pro Asn Ile Ile Arg Leu Glu Gly Val Val Thr Lys Ser
690                 695                 700

Arg Pro Val Met Ile Leu Thr Glu Phe Met Glu Asn Cys Ala Leu Asp
705                 710                 715                 720

Ser Phe Leu Arg Leu Asn Asp Gly Gln Phe Thr Val Ile Gln Leu Val
                725                 730                 735

Gly Met Leu Arg Gly Ile Ala Ala Gly Met Lys Tyr Leu Ser Glu Met
                740                 745                 750

Asn Tyr Val His Arg Asp Leu Ala Ala Arg Asn Ile Leu Val Asn Ser
        755                 760                 765

Asn Leu Val Cys Lys Val Ser Asp Phe Gly Leu Ser Arg Phe Leu Glu
770                 775                 780

Asp Asp Pro Ser Asp Pro Thr Tyr Thr Ser Ser Leu Gly Gly Lys Ile
785                 790                 795                 800

Pro Ile Arg Trp Thr Ala Pro Glu Ala Ile Ala Tyr Arg Lys Phe Thr
                805                 810                 815

Ser Ala Ser Asp Val Trp Ser Tyr Gly Ile Val Met Trp Glu Val Met
                820                 825                 830

Ser Tyr Gly Glu Arg Pro Tyr Trp Asp Met Ser Asn Gln Asp Val Ile
        835                 840                 845

Asn Ala Val Glu Gln Asp Tyr Arg Leu Pro Pro Met Asp Cys Pro
850                 855                 860

Thr Ala Leu His Gln Leu Met Leu Asp Cys Trp Val Arg Asp Arg Asn
865                 870                 875                 880

Leu Arg Pro Lys Phe Ser Gln Ile Val Asn Thr Leu Asp Lys Leu Ile
                885                 890                 895

Arg Asn Ala Ala Ser Leu Lys Val Ile Ala Ser Ala Gln Ser Gly Met
                900                 905                 910

Ser Gln Pro Leu Leu Asp Arg Thr Val Pro Asp Tyr Thr Thr Phe Thr
        915                 920                 925

Thr Val Gly Asp Trp Leu Asp Ala Ile Lys Met Gly Arg Tyr Lys Glu
        930                 935                 940

Ser Phe Val Ser Ala Gly Phe Ala Ser Phe Asp Leu Val Ala Gln Met
945                 950                 955                 960
```

```
Thr Ala Glu Asp Leu Leu Arg Ile Gly Val Thr Leu Ala Gly His Gln
            965                 970                 975

Lys Lys Ile Leu Ser Ser Ile Gln Asp Met Arg Leu Gln Met Asn Gln
        980                 985                 990

Thr Leu Pro Val Gln Val
        995

<210> SEQ ID NO 2
<211> LENGTH: 3805
<212> TYPE: DNA
<213> ORGANISM: Homo sapiens

<400> SEQUENCE: 2
```

| | | | | | |
|---|---|---|---|---|---|
| ggctcggctc | ctagagctgc | cacggccatg | ccagagccc | cccgccgcc | gccgccgtcg | 60 |
| ccgccgccgg | ggcttctgcc | gctgctccct | ccgctgctgc | tgctgccgct | gctgctgctg | 120 |
| cccgccggct | gccgggcgct | ggaagagacc | ctcatggaca | caaaatgggt | aacatctgag | 180 |
| ttggcgtgga | catctcatcc | agaaagtggg | tgggaagagg | tgagtggcta | cgatgaggcc | 240 |
| atgaatccca | tccgcacata | ccaggtgtgt | aatgtgcgcg | agtcaagcca | gaacaactgg | 300 |
| cttcgcacgg | ggttcatctg | gcggcgggat | gtgcagcggg | tctacgtgga | gctcaagttc | 360 |
| actgtgcgtg | actgcaacag | catccccaac | atccccggct | cctgcaagga | gaccttcaac | 420 |
| ctcttctact | acgaggctga | cagcgatgtg | gcctcagcct | cctccccctt | ctggatggag | 480 |
| aaccccctacg | tgaaagtgga | caccattgca | cccgatgaga | gcttctcgcg | gctggatgcc | 540 |
| ggccgtgtca | acaccaaggt | gcgcagcttt | gggccacttt | ccaaggctgg | cttctacctg | 600 |
| gccttccagg | accagggcgc | ctgcatgtcg | ctcatctccg | tgcgcgcctt | ctacaagaag | 660 |
| tgtgcatcca | ccaccgcagg | cttcgcactc | ttccccgaga | ccctcactgg | ggcggagccc | 720 |
| acctcgctgg | tcattgctcc | tggcacctgc | atccctaacg | ccgtggaggt | gtcggtgcca | 780 |
| ctcaagctct | actgcaacgg | cgatggggag | tggatggtgc | ctgtgggtgc | ctgcacctgt | 840 |
| gccaccggcc | atgagccagc | tgccaaggag | tcccagtgcc | gcccctgtcc | cctgggagc | 900 |
| tacaaggcga | agcagggaga | ggggccctgc | ctccccatgtc | ccccaacag | ccgtaccacc | 960 |
| tccccagccg | ccagcatctg | cacctgccac | aataacttct | accgtgcaga | ctcggactct | 1020 |
| gcggacagtg | cctgtaccac | cgtgccatct | ccaccccgag | gtgtgatctc | caatgtgaat | 1080 |
| gaaacctcac | tgatcctcga | gtggagtgag | ccccgggacc | tgggtgtccg | ggatgacctc | 1140 |
| ctgtacaatg | tcatctgcaa | gagtgccat | ggggctggag | gggcctcagc | tgctcacgc | 1200 |
| tgtgatgaca | cgtggagtt | tgtgcctcgg | cagctgggcc | tgtcggagcc | ccgggtccac | 1260 |
| accagccatc | tgctggccca | cacgcgctac | acctttgagg | tgcaggcggt | caacggtgtc | 1320 |
| tcgggcaaga | gccctctgcc | gcctcgttat | gcggccgtga | atatcaccac | aaaccaggct | 1380 |
| gccccgtctg | aagtgcccac | actacgcctg | cacagcagct | caggcagcag | cctcaccta | 1440 |
| tcctgggcac | cccagagcg | gcccaacgga | gtcatcctgg | actacgagat | gaagtacttt | 1500 |
| gagaagagcg | agggcatcgc | ctccacagtg | accagccaga | tgaactccgt | gcagctggac | 1560 |
| gggcttcggc | ctgacgcccg | ctatgtggtc | caggtccgtg | cccgcacagt | agctggctat | 1620 |
| ggcagtaca | gccgccctgc | cgagtttgag | accacaagtg | agagaggctc | tggggcccag | 1680 |
| cagctccagg | agcagcttcc | cctcatcgtg | ggctccgcta | cagctgggct | tgtcttcgtg | 1740 |
| gtggctgtcg | tggtcatcgc | tatcgtctgc | tcaggaagc | agcgacacgg | ctctgattcg | 1800 |
| gagtacacgg | agaagctgca | gcagtacatt | gctcctggaa | tgaaggttta | tattgaccct | 1860 |

-continued

```
tttacctacg aggaccctaa tgaggctgtt cgggagtttg ccaaggagat cgacgtgtcc    1920
tgcgtcaaga tcgaggaggt gatcggagct ggggaatttg gggaagtgtg ccgtggtcga    1980
ctgaaacagc ctggccgccg agaggtgttt gtggccatca agacgctgaa ggtgggctac    2040
accgagaggc agcggcggga cttcctaagc gaggcctcca tcatgggtca gtttgatcac    2100
cccaatataa tccggctcga gggcgtggtc accaaaagtc ggccagttat gatcctcact    2160
gagttcatgg aaaactgcgc cctggactcc ttcctccggc tcaacgatgg gcagttcacg    2220
gtcatccagc tggtgggcat gttgcggggc attgctgccg gcatgaagta cctgtccgag    2280
atgaactatg tgcaccgcga cctggctgct cgcaacatcc ttgtcaacag caacctggtc    2340
tgcaaagtct cagactttgg cctctcccgc ttcctggagg atgacccctc cgatcctacc    2400
tacaccagtt ccctgggcgg gaagatcccc atccgctgga ctgccccaga ggccatagcc    2460
tatcggaagt tcacttctgc tagtgatgtc tggagctacg gaattgtcat gtgggaggtc    2520
atgagctatg gagagcgacc ctactgggac atgagcaacc aggatgtcat caatgccgtg    2580
gagcaggatt accggctgcc accacccatg gactgtccca cagcactgca ccagctcatg    2640
ctggactgct gggtgcggga ccggaacctc aggcccaaat tctcccagat tgtcaatacc    2700
ctggacaagc tcatccgcaa tgctgccagc ctcaaggtca ttgccagcgc tcagtctggc    2760
atgtcacagc cctcctgga ccgcacggtc ccagattaca caaccttcac gacagttggt    2820
gattggctgg atgccatcaa gatggggcgg tacaaggaga gcttcgtcag tgcggggttt    2880
gcatcttttg acctggtggc ccagatgacg gcagaagacc tgctccgtat tggggtcacc    2940
ctggccggcc accagaagaa gatcctgagc agtatccagg acatgcggct gcagatgaac    3000
cagacgctgc ctgtgcaggt ctgacaccgg ctcccacggg gaccctgagg accgtgcagg    3060
gatgccaagc agccggctgg actttcggac tcttggactt ttggatgcct ggccttaggc    3120
tgtggcccag aagctggaag tttgggaaag gcccaagctg ggacttctcc aggcctgtgt    3180
tccctcccca ggaagtgcgc cccaaacctc ttcatattga agatggatta ggagaggggg    3240
tgatgacccc tccccaagcc cctcaggggc cagaccttcc tgctctccag caggggatcc    3300
ccacaacctc acacttgtct gttcttcagt gctggaggtc ctggcagggt caggctgggg    3360
taagccgggg ttccacaggg cccagccctg gcagggtct ggcccccag gtaggcggag     3420
agcagtccct ccctcaggaa ctggaggagg ggactccagg aatggggaaa tgtgacacca    3480
ccatcctgaa gccagcttgc acctccagtt tgcacaggga tttgtcctgg gggctgaggg    3540
ccctgtcccc accccgccc ttggtgctgt cataaaaggg caggcagggg caggctgagg     3600
agttgcccgt tgccccccag agactgactc tcagagccag agatgggatg tgtgagtgtg    3660
tgtgtgtgtg tgtgcgcgcg cgcgcgcgtg tgtgtgtgca cgcactggcc tgcacagaga    3720
gcatgggtga gcgtgtaaaa gcttggccct gtgccctaca gtggggacag ctgggccgac    3780
agcagaataa aggcaataag atgaa                                          3805
```

<210> SEQ ID NO 3
<211> LENGTH: 22
<212> TYPE: DNA
<213> ORGANISM: Homo sapiens

<400> SEQUENCE: 3
actgatcctc gagtggagtg ag                                              22

<210> SEQ ID NO 4
<211> LENGTH: 22

-continued

```
<212> TYPE: DNA
<213> ORGANISM: Homo sapiens

<400> SEQUENCE: 4
cacctcaaag gtgtagcgcg tg                                              22

<210> SEQ ID NO 5
<211> LENGTH: 19
<212> TYPE: DNA
<213> ORGANISM: Homo sapiens

<400> SEQUENCE: 5
ctcggctcct agagctgcc                                                  19

<210> SEQ ID NO 6
<211> LENGTH: 19
<212> TYPE: DNA
<213> ORGANISM: Homo sapiens

<400> SEQUENCE: 6
ctgcttggca tccctgcac                                                  19

<210> SEQ ID NO 7
<211> LENGTH: 15
<212> TYPE: PRT
<213> ORGANISM: Homo sapiens

<400> SEQUENCE: 7

Gly Gln Tyr Ser Arg Pro Ala Glu Phe Glu Thr Thr Ser Glu Arg
1               5                   10                  15

<210> SEQ ID NO 8
<211> LENGTH: 13
<212> TYPE: PRT
<213> ORGANISM: Homo sapiens

<400> SEQUENCE: 8

Cys Ala Thr Gly His Glu Pro Ala Ala Lys Glu Ser Gln
1               5                   10

<210> SEQ ID NO 9
<211> LENGTH: 17
<212> TYPE: PRT
<213> ORGANISM: Homo sapiens

<400> SEQUENCE: 9

Gly Gln Tyr Ser Arg Pro Ala Glu Phe Glu Thr Thr Ser Glu Arg Gly
1               5                   10                  15
Ser
```

EPHRIN-B RECEPTOR PROTEIN INVOLVED IN CARCINOMA

The present application is a National Stage Application claiming the priority of co-pending PCT Application No. PCT/GB2003/001593 filed Apr. 9, 2003, which in turn, claims priority from Great Britain Application Serial No. 0208089.3, filed Apr. 9, 2002. Applicants claim the benefits of 35 U.S.C. § 120 as to the PCT application and priority under 35 U.S.C. § 119 as to the said Great Britain application, and the entire disclosures of both applications are incorporated herein by reference in their entireties.

The present invention relates to the use of the protein CCMP-1/ephrin B-type 3 receptor, compositions comprising the protein, including vaccines and antibodies that are immunospecific for the protein, in the diagnosis, prophylaxis and treatment of carcinoma.

Excluding skin cancers, colorectal cancer is the third most common cancer diagnosed in men and women in the United States. Survival rates for those people whose colorectal cancer is found and treated in an early stage are good, but only 37% of colorectal cancers are found at that early stage. Once the cancer has spread to nearby organs or lymph nodes, the 5-year relative survival rate significantly decreases. Carcinoembryonic antigen (CEA) and CA 19-9 are substances produced by cells of most colon and rectal cancers and released into the bloodstream. These markers, however, can be high for reasons other than cancer, or can be normal in a person who has cancer. Thus, a need exists for more specific markers of colorectal cancer.

There are no generally approved immunotherapeutic drugs for the treatment of colorectal cancer, despite the fact that immunotherapy may offer the greatest potential after surgical resection in the adjuvant setting. Edrecolomab (monoclonal antibody 17-1A, or Panorex™), however, is an adjunctive therapy for colorectal cancer which is in clinical trials in the UK and the US, and which has already been approved in Germany. Identification of new suitable targets or antigens for immunotherapy of colorectal cancer is therefore highly important.

Breast cancer is one of the leading causes of cancer death for women in the Western world. The major challenges in breast cancer treatment are to improve early detection rates, to find new non-invasive markers that can be used to follow disease progression and identify relapse, and to find improved and less toxic therapies, especially for more advanced disease where 5 year survival is still very poor. There is a great need to identify targets which are more specific to the cancer cells, ideally ones which are expressed on the surface of the tumour cells so that they can be attacked bypproaches such as immunotherapeutics and targeted toxins.

Tumour specific proteins have been identified for a number of cancer types using techniques such as differential screening of cDNAs (Hubert, R. S., et al., 1999, Proc. Natl. Acad. Sci. USA 96, 14523-14528) and the purification of cell-surface proteins that are recognised by tumour-specific antibodies (Catimel, B., et al., 1996, J. Biol. Chem. 271, 25664-25670). More recently, DNA 'chips' containing up to 10,000 expressed sequence elements have been used to characterise tumour cell gene expression Dhanasekaran, S. M., et al., 2001, Nature 412, 822-826). However, there are several reasons why the numerous and extensive previous transcriptomic analysis of cancers may not have revealed all, or even most, tumour associated proteins. These include:

(i) a lack of correlation between transcript and disease-associated protein levels; particularly common for membrane proteins that often have a long half-life and as such do not have a high mRNA turnover. Therefore, whilst the difference in protein levels between normal and cancerous cells are consistent it is often difficult to associate changes in the mRNA for a given membrane protein with the cancerous state;

(ii) translocation of a protein in the disease state rather than simply differential levels of the transcript, for example, erbB2/HER2-neu, shows much greater plasma-membrane localisation in cancer cells than normal breast cells, and the transcription factors oestrogen receptor and STAT3 translocate to the nucleus to exert their tumourigenic effects; and (iii) novel/uncharacterised genes are not highly represented within the 'closed system' of a cDNA array where there are restrictions on the number of expressed sequence elements per chip and the knowledge and availability of DNA clones.

As an alternative approach to identifying tumour antigens, the present inventors used proteomics to characterise the complement of proteins in cell membranes isolated from carcinoma cell lines.

CCMP-1 is a receptor tyrosine kinase also known as ephrin B-type receptor 3. At the gene level, cDNA profiling indicates that CCMP-1 is one of fifteen genes overexpressed in prostate cancer tissue, however RT-PCR and Northern blot analysis verified these results in 40% and 88% of genes, respectively, demonstrating the need to better validate quantitative differences in gene expression revealed by array-based techniques (Chaib H. et al., 2001, Neoplasia 3: 43-52). Moderate to low levels of CCMP-1 transcripts have also been demonstrated in three out of four small cell lung carcinoma cell lines (Tang, X. et al., 1998, Proc. Natl. Acad. Sci. USA 95:9779-9784) and differential expression of the ligands for ephrin B-type receptors has been demonstrated with ephrin-B2 having higher expression in the colon carcinoma specimens studied than in adjacent normal mucosa. The ligand ephrin-B2 and ephrin B-type receptor 4 were most frequently expressed on the luminal surface of colon carcinoma epithelium (Liu, W. et al., 2002, Cancer 94: 934-939).

WO 01/57188 provides a large number of cDNA sequences and their encoded proteins. These include a sequence, identified as sequence ID NO:2273, which corresponds to CCMP-1. The sequence was indicated as equivalent to any of the other 1350 sequences identified, as being useful in preventing, treating or ameliorating a condition, such as arthritis or cancer. DE4233782 provides cDNA amplified from RNA isolated from embryonic tissue which encodes a polypeptide 99% identical to CCMP-1. However, these disclosures do not identify CCMP-1 as being localised to the peripheral membrane, nor useful for a therapeutic approach to colorectal cancer or breast cancer.

The prior art does not show a cancer-associated alteration of the CCMP-1 protein and therefore, does not show the usefulness of CCMP-1 in a therapeutic approach to carcinoma, more specifically to tumour cells derived from epithelial cells typically found in the lining of body organs for example, but not limited to, breast, prostate, colon, pancreas, prostate adenocarcinoma, tongue squamous cell carcinoma, larynx squamous cell carcinoma, pharynx squamous cell carcinoma, parotid carcinoma, lung squamous cell carcinoma, and a brain astrocytoma, as well as kidney carcinomas and renal cell carcinomas, bladder carcinoma and a papillary cystadenocarcinoma. The term 'carcinoma' includes a malignant new growth that arises from epithelium, found in skin or, more commonly, the lining of body organs, for example: breast, prostate, lung, stomach or bowel. Carcinomas tend to infiltrate into adjacent tissue and spread (metastasise) to distant organs, for example: to bone, liver, lung or the brain.

The present invention is based on the finding of cancer-associated alterations in the expression of CCMP-1 protein in carcinoma. Thus, the invention provides the use of CCMP-1 for the diagnosis and treatment of carcinoma, for example, but not limited to, breast and colorectal carcinoma.

Thus, in one aspect, the present invention provides a method of screening for and/or diagnosis of carcinoma in a subject, and/or monitoring the effectiveness of carcinoma therapy, which comprises the step of detecting and/or quantifying in a biological sample obtained from said subject:

(i) a CCMP-1 polypeptide which:

a) comprises or consists of the amino acid sequence of SEQ ID NO:1;

b) is a derivative having one or more amino acid substitutions, modifications, deletions or insertions relative to the amino acid sequence of SEQ ID NO: 1 which retains the activity of CCMP-1; or c) is a fragment of a polypeptide having the amino acid sequence of SEQ ID NO: 1, which is at least ten amino acids long and has at least 70% homology over the length of the fragment.

Hereinafter, such polypeptides are referred to as CCMP-1 polypeptides. In order to more fully appreciate the present invention polypeptides within the scope of a)-c), above, will now be discussed in greater detail. It will be apparent to one skilled in the art that peptides for use in the invention include CCMP-1, derivatives, fragments and modified forms (e.g. analogues) thereof.

Polypeptides Within the Scope of a)

A polypeptide within the scope of a), may consist of the particular amino acid sequence given in FIG. 1 (SEQ ID NO:1) or may have an additional N-terminal and/or an additional C-terminal amino acid sequence relative to said sequence. Additional sequences may be provided in order to alter the characteristics of a particular polypeptide. This can be useful in improving recombinant expression or regulation of expression in particular expression systems. For example, an additional sequence may provide some protection against proteolytic cleavage. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag. An additional sequence which may provide stability during recombinant production may also be used. Such sequences may be optionally removed as required by incorporating a cleavable sequence as an additional sequence or part thereof. Thus, a polypeptide may be fused to other moieties including other polypeptides. Such additional sequences and affinity tags are well known in the art.

Thus, additional sequences can also be useful in altering the properties of a polypeptide to aid in identification or purification. For example, a fusion protein may be provided in which a polypeptide is linked to a moiety capable of being isolated by affinity chromatography. The moiety may be an antigen or an epitope and the affinity column may comprise immobilised antibodies or immobilised antibody fragments which bind to said antigen or epitope (desirably with a high degree of specificity). The fusion protein can usually be eluted from the column by addition of an appropriate buffer.

Additional N-terminal or C-terminal sequences may, however, be present simply as a result of a particular technique used to obtain a polypeptide and need not provide any particular advantageous characteristic to the polypeptide. Such polypeptides are within the scope of the present invention.

Whatever additional N-terminal or C-terminal sequence is present, it is preferred that the resultant polypeptide should exhibit the immunological or biological activity of the polypeptide having the amino acid sequence shown in FIG. 1 (SEQ ID NO:1).

Polypeptides Within the Scope of b)

Turning now to the polypeptides defined in b) above, it will be appreciated by the person skilled in the art that these polypeptides are derivatives (or variants) of the polypeptide given in a) above. Such derivatives preferably exhibit the immunological or biological activity of the polypeptide of SEQ ID NO:1. Alternatively, the biological activity of the polypeptide may be altered. As such, it will be appreciated by one skilled in the art that derivatives can include post-translational modifications, for example but without limitation, phosphorylation, glycosylation and farnesylation.

Alterations in the amino acid sequence of a protein can occur which do not affect the function of a protein. These include amino acid deletions, insertions and substitutions and can result from alternative splicing and/or the presence of multiple translational start sites and/or stop sites. Polymorphisms may arise as a result of the infidelity of the translational process. Thus changes in amino acid sequence which do not affect the protein's biological or immunological function may be tolerated.

The skilled person will appreciate that various changes can often be made to the amino acid sequence of a polypeptide which has a particular activity to produce derivatives (sometimes known as variants or "muteins") having at least a proportion of said activity, and preferably having a substantial proportion of said activity. Such derivatives of the polypeptides described in a) above are within the scope of the present invention and include allelic and non-allelic derivatives.

An example of a derivative of the polypeptide for use in the present invention is a polypeptide as defined in a) above, apart from the substitution of one or more amino acids with one or more other amino acids. Amino acid substitutions may be conservative or semi-conservative as known in the art and preferably do not significantly affect the desired activity of the polypeptide. Substitutions may be naturally occurring or may be introduced for example using mutagenesis (e.g. Hutchinson et al., 1978, J. Biol. Chem. 253:6551).

Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic).

Other amino acids which can often be substituted for one another include:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains); and aspartic acid and glutamic acid can substitute for phospho-serine and phospho-threonine, respectively (amino acids with acidic side chains).

Amino acid deletions or insertions may also be made relative to the amino acid sequence given in a) above. Thus, for example, amino acids which do not have a substantial effect on the biological and/or immunological activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced, for example, dosage levels can be reduced.

In a particular embodiment, the substituted amino acid(s) do significantly affect the activity of the CCMP-1 polypeptide and may be selected specifically to render dominant negative activity upon the peptide. In another embodiment, the substituted amino acid(s) may be selected specifically to render the polypeptide constitutively active.

Polypeptides comprising amino acid insertions relative to the sequence given in a) above are also included within the scope of the invention. Such changes may alter the properties of a polypeptide used in the present invention (e.g. to assist in identification, purification or expression, as explained above in relation to fusion proteins). Said amino acid changes can be made using any suitable technique e.g. by using site-directed mutagenesis (Hutchinson et al., 1978, J. Biol. Chem. 253: 6551).

It should be appreciated that amino acid substitutions or insertions to the polypeptide for use in the present invention can be made using naturally occurring or non-naturally occurring amino acids. Whether or not natural or synthetic amino acids are used, it is preferred that only L-amino acids are present.

Whatever amino acid changes are made (whether by means of substitution, modification, insertion or deletion), preferred polypeptides for use in the present invention have at least 50% sequence identity with a polypeptide as defined in a) above, more preferably the degree of sequence identity is at least 75%, at least 80%, at least 85%, at least 90% or at least 95%. Sequence identities of at least 90%, at least 95% or at least 98% are most preferred.

The term identity can be used to describe the similarity between two polypeptide sequences. The degree of amino acid sequence identity can be calculated using a program such as "bestfit" (Smith and Waterman, Advances in Applied Mathematics, 482-489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

A software package well known in the art for carrying out this procedure is the CLUSTAL program. It compares the amino acid sequences of two polypeptides and finds the optimal alignment by inserting spaces in either sequence as appropriate. The amino acid identity or similarity (identity plus conservation of amino acid type) for an optimal alignment can also be calculated using a software package such as BLASTX. This program aligns the largest stretch of similar sequence and assigns a value to the fit. For any one pattern comparison, several regions of similarity may be found, each having a different score. One skilled in the art will appreciate that two polypeptides of different lengths may be compared over the entire length of the longer fragment. Alternatively small regions may be compared. Normally sequences of the same length are compared for a useful comparison to be made.

Where high degrees of sequence identity are present there will be relatively few differences in amino acid sequence. Thus for example they may be less than 20, less than 10, or even less than 5 differences.

Polypeptides Within the Scope of c)

As discussed supra, it is often advantageous to reduce the length of a polypeptide, provided that the resultant reduced length polypeptide still has a desired activity or can give rise to useful antibodies. Feature c) therefore covers fragments of polypeptides a) or b) above for use in the present invention.

The skilled person can determine whether or not a particular fragment has activity using the techniques disclosed above. Preferred fragments are at least 10 amino acids long. They may be at least 20, at least 50, at least 100 amino acids or more long. Any given fragment of a polypeptide may or may not possess a functional activity of the parent polypeptide.

A 'derivative' of a polypeptide includes a polypeptide that comprises an amino acid sequence of a parent polypeptide that has been altered by the introduction of amino acid residue substitutions, deletions or additions, and/or amino acid modifications such as but not limited to, phosphorylation and glycosylation. A derivative also encompasses homologues, analogues and orthologues of a parent polypeptide. The derivative polypeptide preferably possesses a similar or identical function to the parent polypeptide.

One means for detecting/quantifying a CCMP-1 polypeptide of use in the methods of screening and diagnosis disclosed herein, involves the use of an antibody. Thus, CCMP-1 polypeptides also find use in raising antibodies. Preferably, the antibody is used for detecting and/or quantifying the amount of a polypeptide as defined in the first aspect of the invention in a biological sample obtained from said subject.

In one embodiment, binding of antibody in tissue sections can be used to detect aberrant CCMP-1 polypeptide localisation or an aberrant level of a CCMP-1 polypeptide. In a specific embodiment, an antibody recognising a CCMP-1 polypeptide can be used to assay a patient tissue (e.g. a breast biopsy) for the level of the CCMP-1 polypeptide where an aberrant level of the CCMP-1 polypeptide is indicative of carcinoma. An "aberrant level" includes a level that is increased or decreased compared with the level in a subject free from carcinoma or a reference level.

In a further aspect, the method of detecting/quantifying the presence of a CCMP-1 polypeptide comprises detecting the captured polypeptide using a directly or indirectly labelled detection reagent, e.g. a detectable marker such as, without limitation, a chemiluminescent, enzymatic, fluorescent, or radioactive moiety.

The methods of diagnosis according to the present invention may be performed using a number of methods known to those skilled in the art, including, without limitation, immunoprecipitation followed by sodium dodecyl sulfate polyacrylamide gel electrophoresis, 2-dimensional gel electrophoresis, competitive and non-competitive assay systems using techniques such as Western blots, immunocytochemistry, immunohistochemistry, immunoassays, e.g. radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

In the context of the present invention, the biological sample can be obtained from any source, such as a serum sample or a tissue sample, e.g. breast tissue. When looking for evidence of metastasis, one would look at major sites of metastasis such as lymph nodes, liver, lung and/or bone and brain.

The invention also provides diagnostic kits, comprising a capture reagent (e.g. an antibody) against a CCMP-1 polypeptide as defined above. In addition, such a kit may optionally comprise one or more of the following:

(1) instructions for using the capture reagent for diagnosis, prognosis, therapeutic monitoring or any combination of these applications;

(2) a labelled binding partner to the capture reagent;

(3) a solid phase (such as a reagent strip) upon which the capture reagent is immobilised; and (4) a label or insert indicating regulatory approval for diagnostic, prognostic or therapeutic use or any combination thereof.

If no labelled binding partner to the capture reagent is provided, the anti-CCMP-1 polypeptide capture reagent itself can be labelled with a detectable marker (see above).

As will be discussed below, CCMP-1 polypeptides are of use in an immunotherapeutic approach to carcinoma. The skilled person will appreciate that for the preparation of one or more such polypeptides, the preferred approach will be based on recombinant DNA techniques. In addition, nucleic acid molecules encoding the polypeptides or fragments thereof may be used in their own right. Thus, the invention also provides a method of screening for and/or diagnosis of carcinoma in a subject, and/or monitoring the effectiveness of carcinoma therapy which comprises the step of detecting and/or quantifying a nucleic acid molecule in a biological sample obtained from said subject, wherein the nucleic acid molecule:

d) comprises or consists of the DNA sequence of SEQ ID NO: 2 or its RNA equivalent;

e) has a sequence which is complementary to the sequence of d);

f) has a sequence which codes for a CCMP-1 polypeptide as defined in a) to c) above;

g) has a sequence which shows substantial identity with any of those of d), e) and f); or h) is a fragment of d), e), f) or g), which is at least 30 nucleotides in length.

Such nucleic acid molecules described above are hereinafter referred to as CCMP-1 nucleic acids. It is preferred if sequences which show substantial identity with any of those of d) to f) have e.g. at least 50%, at least 75%, at least 80%, at least 85%, at least 90% or 95% and most preferably at least 98% sequence identity. The 'bestfit' program (Smith and Waterman, Advances in applied Mathematics, 482-489 (1981)) is one example of a type of computer software used to find the best segment of similarity between two nucleic acid sequences, whilst the GAP program enables sequences to be aligned along their whole length and finds the optimal alignment by inserting spaces in either sequence as appropriate.

Unless the context indicates otherwise, CCMP-1 nucleic acid molecules may have one or more of the following characteristics:

1) they may be DNA or RNA;

2) they may be single or double stranded;

3) they may be provided in recombinant form, e.g. covalently linked to a 5' and/or a 3' flanking sequence to provide a molecule which does not occur in nature;

4) they may be provided without 5' and/or 3' flanking sequences which normally occur in nature;

5) they may be provided in substantially pure form. Thus they may be provided in a form which is substantially free from contaminating proteins and/or from other nucleic acids; and 6) they may be provided with introns or without introns (e.g. as cDNA).

These CCMP-1 nucleic acid molecules are now discussed in greater detail. The term 'RNA equivalent' above, indicates that a given RNA molecule has a sequence which is complementary to that of a given DNA molecule, allowing for the fact that in RNA 'U' replaces 'T' in the genetic code. The nucleic acid molecule may be in isolated, recombinant or chemically synthetic form.

In addition to CCMP-1 nucleic acid molecules coding for CCMP-1 polypeptides, referred to herein as "coding" nucleic acid molecules, complementary nucleic acids are also included. Thus, for example, both strands of a double stranded nucleic acid molecule are included in the present invention (whether or not they are associated with one another). Also included are mRNA molecules and complementary DNA molecules (e.g. cDNA molecules).

The use of nucleic acid molecules which can hybridise to any of the CCMP-1 nucleic acid molecules discussed above is also covered by the present invention. Such nucleic acid molecules are referred to herein as "hybridising" nucleic acid molecules. Hybridising nucleic acid molecules can be useful as probes or primers, for example, or in hybridisation assays.

Hybridisation assays can be used for detection, prognosis, diagnosis, or monitoring of conditions, disorders, or disease states, associated with aberrant expression of genes encoding a CCMP-1 polypeptide, or for differential diagnosis of patients with signs or symptoms suggestive of carcinoma. In particular, such a hybridisation assay can be carried out by a method comprising contacting a patient sample containing nucleic acid with a nucleic acid probe capable of hybridising to a CCMP-1 DNA or RNA that encodes a CCMP-1 polypeptide, under conditions such that hybridisation can occur, and detecting or measuring any resulting hybridisation. Accordingly, such a hybridisation assay comprises:

i) contacting a biological sample, obtained from a subject, containing nucleic acid with a nucleic acid probe capable of hybridising to a CCMP-1 nucleic acid molecule, under conditions such that hybridisation can occur; and ii) detecting or measuring any resulting hybridisation.

Desirably such hybridising molecules are at least 10 nucleotides in length and preferably are at least 25 or at least 50 nucleotides in length. The hybridising nucleic acid molecules preferably hybridise to nucleic acids within the scope of d), e), f), g) or h) above, specifically.

Desirably the hybridising molecules will hybridise to such molecules under stringent hybridisation conditions. One example of stringent hybridisation conditions is where attempted hybridisation is carried out at a temperature of from about 35° C. to about 65° C. using a salt solution which is about 0.9M. However, the skilled person will be able to vary such conditions as appropriate in order to take into account variables such as probe length, base composition, type of ions present, etc. For a high degree of selectivity, relatively stringent conditions are used to form the duplexes, such as low salt or high temperature conditions. As used herein, "highly stringent conditions" means hybridisation to filter-bound DNA in 0.5 M $NaHPO_4$, 7% sodium dodecyl sulphate (SDS), 1 mM EDTA at 65° C., and washing in 0.1×SSC/0.1% SDS at 68° C. (Ausubel F. M. et al., eds., 1989, Current Protocols in Molecular Biology, Vol. 1, Green Publishing Associates, Inc., and John Wiley & Sons, Inc., New York, at p. 2.10.3). For some applications, less stringent conditions for duplex formation are required. As used herein "moderately stringent conditions" means washing in 0.2×SSC/0.1% SDS at 42° C. (Ausubel et al., 1989, supra). Hybridisation conditions can also be rendered more stringent by the addition of increasing amounts of formamide, to destabilise the hybrid duplex. Thus, particular hybridisation conditions can be readily manipulated, and will generally be chosen depending on the desired results. In general, convenient hybridisation temperatures in the presence of 50% formamide are: 42° C. for a probe which is 95 to 100% identical to the fragment of a gene encoding a polypeptide as defined herein, 37° C. for 90 to 95% identity and 32° C. for 70 to 90% identity.

The invention also provides a kit comprising a nucleic acid probe capable of hybridising to CCMP-1 RNA encoding a CCMP-1 polypeptide. In a specific embodiment, a kit comprises in one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding a polypeptide as defined herein, such as by polymerase chain reaction (see e.g. Innis et al., 1990, PCR Protocols, Academic Press, Inc., San Diego, Calif.), ligase chain reaction (see EP320, 308) use of Qβ replicase, cyclic probe reaction, or other methods known in the art.

A hybridising nucleic acid molecule of use in the present invention may have a high degree of sequence identity along its length with a nucleic acid molecule within the scope of d)-h) above (e.g. at least 50%, at least 75%, at least 80%, at least 85%, at least 90%, 95%, or at least 98% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

If desired, a gene encoding a CCMP-1 polypeptide, a related gene, or related CCMP-1 nucleic acid sequence or sub-sequence, including complementary sequences, can also be used in hybridisation assays. A CCMP-1 nucleotide encoding a CCMP-1 polypeptide, or sub-sequences thereof comprising at least 8 nucleotides, can be used as a hybridisation probe.

In another aspect, the present invention provides a method for the prophylaxis and/or treatment of carcinoma in a subject, which comprises administering to said subject a therapeutically effective amount of at least one CCMP-1 polypeptide.

In a yet another aspect, the present invention provides the use of at least one CCMP-1 polypeptide in the preparation of a pharmaceutical composition for use in the prophylaxis and/or treatment of carcinoma. The subject may be a mammal and is preferably a human.

In a particular embodiment, a CCMP-1 polypeptide is fused to another polypeptide, such as the protein transduction domain of the HIV/Tat protein, which facilitates the entry of the fusion protein into a cell (Asoh, S. et al., 2002, Proc. Natl. Acad. Sci. USA, 99:17107-17112), is provided for use in the manufacture of a pharmaceutical composition for the treatment of carcinoma.

Recombinant CCMP-1 polypeptides may be prepared by processes well known in the art from genetically engineered host cells comprising expression systems. Accordingly, the present invention also relates to expression systems which comprise a CCMP-1 polypeptide or CCMP-1 nucleic acid, to host cells which are genetically engineered with such expression systems and to the production of CCMP-1 polypeptides by recombinant techniques. Cell-free translation systems systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK.

For recombinant CCMP-1 polypeptide production, host cells can be genetically engineered to incorporate expression systems or portions thereof for CCMP-1 nucleic acids.

Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, $2^{nd}$ Ed., Cold Spring Harbour laboratory Press, Cold Spring Harbour, N.Y., 1989).

Representative examples of host cells include bacterial cells e.g. *E. Coli, Streptococci, Staphylococci, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, HEK293, BHK and Bowes melanoma cells; and plant cells.

A wide variety of expression systems can be used, such as and without limitation, chromosomal, episomal and virus-derived systems, e.g. vectors derived from bacterial plasmids, from bacteriophage, from transposons, from yeast episomes, from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a nucleic acid to produce a polypeptide in a host may be used. The appropriate CCMP-1 nucleic acid sequence may be inserted into an expression system by any variety of well-known and routine techniques, such as those set forth in Sambrook et al., supra. Appropriate secretion signals may be incorporated into the CCMP-1 polypeptide to allow secretion of the translated protein into the lumen of the endoplasmic reticulum, the periplasmic space or the extracellular environment. These signals may be endogenous to the CCMP-1 polypeptide or they may be heterologous signals.

In one embodiment, CCMP-1 polypeptides are provided in isolated form and include CCMP-1 polypeptides that have been purified to at least some extent and may be fused to other moieties. CCMP-1 polypeptides can be produced using recombinant methods, synthetically produced or produced by a combination of these methods. In particular, fusions of the CCMP-1 polypeptides with localisation-reporter proteins such as the Green Fluorescent Protein (U.S. Pat. Nos. 5,625, 048, 5,777,079, 6,054,321 and 5,804,387) or the DsRed fluorescent protein (Matz, et al., 1999, Nature Biotech. 17:969-973) are specifically contemplated. CCMP-1 polypeptides may be provided in substantially pure form, that is to say free, to a substantial extent, from other proteins. Thus, a CCMP-1 polypeptide may be provided in a composition in which it is the predominant component present (i.e. it is present at a level of at least 50%; preferably at least 75%, at least 80%, at least 85%, at least 90%, or at least 95%; when determined on a weight/weight basis excluding solvents or carriers).

If a CCMP-1 polypeptide is to be expressed for use in cell-based screening assays as discussed later, it is preferred that the polypeptide be produced at the cell surface. In this event, the cells may be harvested prior to use in the screening assay. If the CCMP-1 polypeptide is secreted into the medium, the medium can be recovered in order to isolate said polypeptide. If produced intracellularly, the cells must first be lysed before the CCMP-1 polypeptide is recovered.

CCMP-1 polypeptides can be recovered and purified from recombinant cell cultures by well-known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to a CCMP-1 polypeptide can be used to deplete a sample comprising a CCMP-1 polypeptide of said polypeptide or to purify said polypeptide. Techniques well-known in the art, may be used for refolding to regenerate native or active conformations of the CCMP-1 polypeptides when the polypeptides have been denatured during isolation and or purification.

In a further aspect, the present invention provides a method for the prophylaxis and/or treatment of carcinoma in a subject, which comprises administering to said subject a therapeutically effective amount of at least one CCMP-1 nucleic acid.

In yet another embodiment, the present invention provides the use of at least one CCMP-1 nucleic acid in the preparation of a pharmaceutical composition for use in the treatment of carcinoma.

In a specific embodiment, hybridising nucleic acid molecules are used as anti-sense molecules, to alter the expression of CCMP-1 polypeptides by binding to complementary CCMP-1 nucleic acids and can be used in the treatment or prevention of carcinoma. An anti-sense nucleic acid includes a CCMP-1 nucleic acid capable of hybridising by virtue of some sequence complementarity to a portion of an RNA (preferably mRNA) encoding a CCMP-1 polypeptide. The anti-sense nucleic acid can be complementary to a coding and/or non-coding region of an mRNA encoding such a polypeptide. Most preferably, expression of a CCMP-1 polypeptide is inhibited by use of anti-sense nucleic acids. Thus, the present invention provides the therapeutic or prophylactic use of nucleic acids comprising at least eight nucleotides that are anti-sense to a gene or cDNA encoding a CCMP-1 polypeptide.

In one embodiment, the CCMP-1 nucleic acid is administered via gene therapy (see for example Hoshida, T. et al., 2002, Pancreas, 25:111-121; Ikuno, Y. 2002, Invest. Ophthalmol. Vis. Sci. 2002 43:2406-2411; Bollard, C., 2002, Blood 99:3179-3187; Lee E., 2001, Mol. Med. 7:773-782). Gene therapy refers to administration to a subject of an expressed or expressible nucleic acid. Any of the methods for gene therapy available in the art can be used according to the present invention. In one aspect, the CCMP-1 nucleic acid can be administered as a pharmaceutical composition, said nucleic acid being part of an expression vector that expresses a CCMP-1 polypeptide or chimeric protein thereof in a suitable host. In particular, such a nucleic acid has a promoter operably linked to the polypeptide coding region, said promoter being inducible or constitutive (and, optionally, tissue-specific). In another particular embodiment, a CCMP-1 nucleic acid molecule is used in which the coding sequences and any other desired sequences are flanked by regions that promote homologous recombination at a desired site in the genome, thus providing for intrachromosomal expression of the nucleic acid (Koller & Smithies, 1989, Proc. Natl. Acad. Sci. USA 86:8932-8935; Zijlstra et al., 1989, Nature 342:435-438).

Delivery of the CCMP-1 nucleic acid into a patient may be direct, in which case the patient is directly exposed to the nucleic acid or nucleic acid-carrying vector; this approach is known as in vivo gene therapy. Alternatively, delivery of the nucleic acid into the patient may be indirect, in which case cells are first transformed with the nucleic acid in vitro and then transplanted into the patient; this approach is known as ex vivo gene therapy.

Symptoms of carcinoma may be ameliorated by decreasing the level or activity of a CCMP-1 polypeptide by using gene sequences encoding a polypeptide as defined herein in conjunction with well-known gene "knock-out," ribozyme or triple helix methods to decrease gene expression of the polypeptide. In this approach, ribozyme or triple helix molecules are used to modulate the activity, expression or synthesis of the gene, and thus to ameliorate the symptoms of carcinoma. Such molecules may be designed to reduce or inhibit expression of a mutant or non-mutant target gene. Techniques for the production and use of such molecules are well known to those of skill in the art.

Endogenous CCMP-1 polypeptide expression can also be reduced by inactivating or "knocking out" the gene encoding the polypeptide, or the promoter of such a gene, using targeted homologous recombination (e.g. see Smithies, et al., 1985, Nature 317:230-234; Thomas & Capecchi, 1987, Cell 51:503-512; Thompson et al., 1989, Cell 5:313-321; and Zijistra et al., 1989, Nature 342:435-438). For example, a mutant gene encoding a non-functional polypeptide (or a completely unrelated DNA sequence) flanked by DNA homologous to the endogenous gene (either the coding regions or regulatory regions of the gene encoding the polypeptide) can be used, with or without a selectable marker and/or a negative selectable marker, to transfect cells that express the target gene in viva Insertion of the DNA construct, via targeted homologous recombination, results in inactivation of the target gene.

CCMP-1 nucleic acids may be obtained using standard cloning and screening techniques, from a cDNA library derived from mRNA in human cells, using expressed sequence tag (EST) analysis (Adams, M. et al., 1991, Science, 252:1651-1656; Adams, M. et al., 1992, Nature 355: 632-634; Adams, M. et al., 1995, Nature, 377:Suppl: 3-174). CCMP-1 nucleic acids can also be obtained from natural sources such as genomic DNA libraries or can be synthesized using well known and commercially available techniques. The CCMP-1 nucleic acids comprising coding sequence for CCMP-1 polypeptides can be used for the recombinant production of said polypeptides. The CCMP-1 nucleic acids may include the coding sequence for the mature polypeptide, by itself; or the coding sequence for the mature polypeptide in reading frame with other coding sequences, such as those encoding a leader or secretory sequence, a pre-, pro- or pre-pro-protein sequence, a cleavable sequence or other fusion peptide portions, such as an affinity tag or an additional sequence conferring stability during production of the polypeptide. Preferred affinity tags include multiple histidine residues (for example see Gentz et al., 1989, Proc. Natl. Acad. Sci USA 86:821-824), a FLAG tag, HA tag or myc tag. The CCMP-1 nucleic acids may also contain non-coding 5' and 3' sequences, such as transcribed, non-translated sequences, splicing and polyadenylation signals, ribosome binding sites and sequences that stabilize mRNA.

In the preparation of genomic libraries, DNA fragments are generated, some of which will encode parts or the whole of a polypeptide as defined herein. The DNA may be cleaved at specific sites using various restriction enzymes. Alternatively, one may use DNAse in the presence of manganese to fragment the DNA, or the DNA can be physically sheared, as for example, by sonication. The DNA fragments can then be separated according to size by standard techniques, including but not limited to agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, and yeast artificial chromosomes (YACs) (see, for example, Sambrook et al., 1989, Molecular Cloning, A Laboratory Manual, 1D Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II; Ausubel F. M. et al., eds., 1989, Current Protocols in Molecular Biology, Vol. I, Green Publishing Associates, Inc., and John Wiley & sons, Inc., New York). The genomic library may be screened by nucleic acid hybridisation to labelled probe (Benton & Davis, 1977, Science 196:180; Grunstein & Hogness, 1975, Proc. Natl. Acad. Sci. U.S.A. 72:3961).

Manipulation of the DNA encoding a protein is a particularly powerful technique for both modifying proteins and for generating large quantities of protein for purification purposes. This may involve the use of PCR techniques to amplify a desired nucleic acid sequence. Thus the sequence data provided herein can be used to design primers for use in PCR so that a desired sequence can be targeted and then amplified to a high degree.

Typically, primers will be at least five nucleotides long and will generally be at least ten nucleotides long (e.g. fifteen to twenty-five nucleotides long). In some cases, primers of at least thirty or at least thirty-five nucleotides in length may be used.

As a further alternative, chemical synthesis which may be automated may be used. Relatively short sequences may be chemically synthesised and ligated together to provide a longer sequence.

CCMP-1 polypeptide derivatives as referred to in part b) above can be created by introducing one or more nucleotide substitutions, additions or deletions into the nucleotide sequence of a CCMP-1 nucleic acid such that one or more amino acid substitutions, additions or deletions are introduced into the encoded protein. Standard techniques known to those of skill in the art can be used to introduce mutations, including, for example, site-directed mutagenesis and PCR-mediated mutagenesis. Preferably, conservative amino acid substitutions are made at one or more predicted non-essential amino acid residues.

A CCMP-1 nucleic acid encoding a CCMP-1 polypeptide, including homologues and orthologues from species other than human, may be obtained by a process which comprises the steps of screening an appropriate library under stringent hybridisation conditions with a labelled probe having the sequence of a CCMP-1 nucleic acid as described in d)-h) above, and isolating full-length cDNA and genomic clones containing said nucleic acid sequence. Such hybridisation techniques are well-known in the art and examples of hybridisation conditions are described, supra.

One skilled in the art will understand that, in many cases, an isolated cDNA sequence will be incomplete, in that the region coding for the polypeptide is cut short at the 5' end of the cDNA. This is a consequence of reverse transcriptase, an enzyme with inherently low processivity (a measure of the ability of the enzyme to remain attached to the template during the polymerization reaction), failing to complete a DNA copy of the mRNA template during $1^{st}$ strand cDNA synthesis.

Methods to obtain full length cDNAs or to extend short cDNAs are well known in the art, for example RACE (Rapid amplification of cDNA ends; e.g. Frohman et al., 1988, Proc. Natl. Acad. Sci USA 85:8998-9002). Recent modifications of the technique, exemplified by the Marathon™ technology (Clontech Laboratories Inc.) have significantly simplified the search for longer cDNAs. This technology uses cDNAs prepared from mRNA extracted from a chosen tissue followed by the ligation of an adaptor sequence onto each end. PCR is then carried out to amplify the missing 5' end of the cDNA using a combination of gene specific and adaptor specific oligonucleotide primers. The PCR reaction is then repeated using nested primers which have been designed to anneal with the amplified product, typically an adaptor specific primer that anneals further 3' in the adaptor sequence and a gene specific primer that anneals further 5' in the known gene sequence. The products of this reaction can then be analysed by DNA sequencing and a full length cDNA constructed either by joining the product directly to the existing cDNA to give a complete sequence, or carrying out a separate full length PCR using the new sequence information for the design of the 5' primer.

A further aspect of the invention relates to a vaccine composition of use in the treatment of carcinoma. Thus, a CCMP-1 polypeptide or CCMP-1 nucleic acid may be useful as antigenic material, and may be used in the production of vaccines for treatment or prophylaxis of carcinoma. Such material can be "antigenic" and/or "immunogenic". Generally, "antigenic" is taken to mean that the protein or nucleic acid is capable of being used to raise antibodies or indeed is capable of inducing an antibody response in a subject. "Immunogenic" is taken to mean that the protein or nucleic acid is capable of eliciting a protective immune response in a subject. Thus, in the latter case, the CCMP-1 polypeptide or nucleic acid may be capable of not only generating an antibody response but, in addition, non-antibody based immune responses.

It is well known that is possible to screen an antigenic protein or polypeptide to identify epitopic regions, i.e. those regions which are responsible for the protein or polypeptide's antigenicity or immunogenicity. Amino acid and peptide characteristics well known to the skilled person can be used to predict the antigenic index (a measure of the probability that a region is antigenic) of a CCMP-1 polypeptide. For example, but without limitation, the 'Peptidestructure' program (Jameson and Wolf, 1988, CABIOS, 4(1):181) and a technique referred to as 'Threading' (Altuvia Y. et al., 1995, J. Mol. Biol. 249:244) can be used. Thus, the CCMP-1 polypeptides may include one or more such epitopes or be sufficiently similar to such regions so as to retain their antigenic/immunogenic properties. Methods well known to the skilled person can be used to test fragments and/or homologues and/or derivatives of a polypeptide for antigenicity. Thus, the fragments for use in the present invention may include one or more such epitopic regions or be sufficiently similar to such regions to retain their antigenic/immunogenic properties. Thus, for fragments for use according to the present invention the degree of identity is perhaps irrelevant, since they may be 100% identical to a particular part of a protein or polypeptide, homologue or derivative as described herein. The key issue may be that the fragment retains the antigenic/immunogenic properties of the protein from which it is derived.

CCMP-1 derivatives preferably possess at least a degree of the antigenicity and/or immunogenicity of the protein or polypeptide from which they are derived.

Thus, in a further aspect, the present invention provides the use of a CCMP-1 polypeptide or a CCMP-1 nucleic acid in the production of a pharmaceutical composition for the treatment or prophylaxis of carcinoma, wherein the composition is a vaccine. The vaccine optionally comprises one or more suitable adjuvants. Examples of adjuvants well-known in the art include inorganic gels, such as aluminium hydroxide, and water-in-oil emulsions, such as incomplete Freund's adjuvant. Other useful adjuvants will be well known to the skilled person.

Since a polypeptide or a nucleic acid may be broken down in the stomach, the vaccine composition is preferably administered parenterally (e.g. subcutaneous, intramuscular, intravenous or intradermal injection).

Accordingly, the present invention provides:

(a) the use of a CCMP-1 polypeptide or CCMP-1 nucleic acid in the preparation of an immunogenic composition, preferably a vaccine for the treatment of carcinoma;

(b) the use of such an immunogenic composition in inducing an immune response in a subject; and (c) a method for the treatment or prophylaxis of carcinoma in a subject, or of vaccinating a subject against carcinoma which comprises the step of administering to the subject an effective amount of a CCMP-1 polypeptide or CCMP-1 nucleic acid, preferably as a vaccine.

In a further aspect, the present invention provides a method for the treatment and/or prophylaxis of carcinoma in a subject comprising administering to said subject, a therapeutically effective amount of at least one antibody that binds to a CCMP-1 polypeptide.

Most preferred are antibodies that bind specifically to CCMP-1 polypeptides. In one embodiment, antibodies which specifically bind to CCMP-1 polypeptides may be used to inhibit the activity of said polypeptides, or target therapeutic agents to the tumour.

Thus, in yet another aspect, the present invention provides the use of an antibody which binds to at least one CCMP-1 polypeptide in the preparation of a pharmaceutical composition for use in the prophylaxis and/or treatment of carcinoma. In particular, the preparation of vaccines and/or compositions comprising or consisting of antibodies is a preferred embodiment of this aspect of the invention.

Accordingly, a CCMP-1 polypeptide may be used as an immunogen to generate antibodies which immunospecifically bind such an immunogen. Antibodies of the invention include, but are not limited to polyclonal, monoclonal, bispecific, humanised or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein includes immunoglobulin molecules and immunologically-active portions of immunoglobulin molecules, i.e. molecules that contain an antigen binding site that specifically binds an antigen. An antibody of the invention recognises a CCMP-1 polypeptide. Preferably, an antibody of the invention specifically binds to a CCMP-1 polypeptide. The immunoglobulin molecules of the invention can be of any class (e.g. IgG, IgE, IgM, IgD and IgA) or subclass of immunoglobulin molecule.

In the production of antibodies, screening for the desired antibody can be accomplished by techniques known in the art, e.g. ELISA (enzyme-linked immunosorbent assay). For example, to select antibodies which recognise a specific domain of a CCMP-1 polypeptide, one may assay generated hybridomas for a product which binds to a polypeptide fragment containing such domain. For selection of an antibody that specifically binds a first polypeptide homologue but which does not specifically bind to (or binds less avidly to) a second polypeptide homologue, one can select on the basis of positive binding to the first polypeptide homologue and a lack of binding to (or reduced binding to) the second polypeptide homologue.

For preparation of monoclonal antibodies (mAbs) directed toward a CCMP-1 polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs in the invention may be cultivated in vitro or in vivo. In an additional embodiment of the invention, monoclonal antibodies can be produced in germ-free animals utilising technology known in the art.

The monoclonal antibodies include, but are not limited to, human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb (see, e.g. U.S. Pat. No. 4,816,567; and U.S. Pat. No. 4,816,397) Humanised antibodies are antibody molecules from non-human species having one or more complementarity determining regions (CDRs) from the non-human species and a framework region from a human immunoglobulin molecule (see, e.g. U.S. Pat. No. 5,585,089).

Chimeric and humanised monoclonal antibodies can be produced by recombinant DNA techniques known in the art, for example using methods described in WO 87/02671; EP184,187; EP171,496; EP173,494; WO 86/01533; U.S. Pat. No. 4,816,567; EP125,023; Better et al., 1988, Science 240: 1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et at, 1986, Bio/Techniques 4:214; U.S. Pat. No. 5,225,539; Jones et at, 1986, Nature 321:552-525; Verhoeyan et at (1988) Science 239:1534; and Beidler et at, 1988, J. Immunol. 141:4053-4060.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunised in the normal fashion with a selected antigen, e.g. all or a portion of a CCMP-1 polypeptide. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies (see Lonberg & Huszar, 1995, Int. Rev. Immunol. 13:65-93). For a detailed discussion of this technology for producing human antibodies and human monoclonal antibodies and protocols for producing such antibodies, see, e.g. U.S. Pat. Nos. 5,625,126; 5,633,425; 5,569,825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognise a selected epitope can be generated using a technique referred to as "guided selection." In this approach, a selected non-human monoclonal antibody, e.g. a mouse antibody, is used to guide the selection of a completely human antibody recognising the same epitope (Jespers et al., 1994, Bio/technology 12:899-903).

The antibodies in the present invention can also be generated using various phage display methods known in the art. In phage display methods, functional antibody domains are displayed on the surface of phage particles which carry the polynucleotide sequences encoding them. In a particular, such phage can be utilised to display antigen binding domains expressed from a repertoire or combinatorial antibody library (e.g. human or murine). Phage expressing an antigen binding domain that binds the antigen of interest can be selected or identified with antigen, e.g. using labelled antigen or antigen bound or captured to a solid surface or bead. Phage used in these methods are typically filamentous phage including fd and M13 binding domains expressed from phage with Fab, Fv or disulphide stabilised Fv antibody domains recombinantly fused to either the phage gene III or gene VIII protein. Phage display methods that can be used to make the antibodies of the present invention include those disclosed in Brinkman et al., 1995, J. Immunol. Methods 182: 41-50; Ames et al., 1995, J. Immunol. Methods 184:177-186; Kettleborough et al., 1994, Eur. J. Immunol. 24:952-958; Persic et al, 1997, Gene 187 9-18; Burton et al., 994, Advances in Immunology 57:191-280; EP0589877; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')2 fragments can also be employed using methods known in the art such as those disclosed in WO 92/22324; Mullinax et al., 1992, Bio/Techniques 12(6):864-869; and Sawai et al., 1995, AJRI 34:26-34; and Better et al., 1988, Science 240:1041-1043.

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., 1993, PNAS 90:7995-7999; and Skerra et al., 1988, Science 240:1038-1040.

The invention further provides bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details for generating bispecific antibodies (see, for example, Suresh et al., 1986, Methods in Enzymology 121:210).

The invention provides functionally-active fragments, derivatives or analogues of the anti-polypeptide immunoglobulin molecules. "Functionally-active" means that the fragment, derivative or analogue is able to elicit anti-anti-idiotype antibodies (i.e. tertiary antibodies) that recognise the same antigen that is recognised by the antibody from which the fragment, derivative or analogue is derived. Specifically, in a preferred embodiment, the antigenicity of the idiotype of the immunoglobulin molecule may be enhanced by deletion of framework and CDR sequences that are C-terminal to the CDR sequence that specifically recognises the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')2 fragments and Fab fragments. Antibody fragments which recognise specific epitopes may be generated by known techniques. F(ab')2 fragments consist of the variable region, the light chain constant region and the CH1 domain of the heavy chain and are generated by pepsin digestion of the antibody molecule. Fab fragments are generated by reducing the disulphide bridges of the F(ab')2 fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in E. coli may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogues and derivatives that are either modified, i.e. by the covalent attachment of any type of molecule as long as such covalent attachment that does not impair immunospecific binding. For example, but not by way of limitation, the derivatives and analogues of the immunoglobulins include those that have been further modified, e.g. by glycosylation, acetylation, pegylation, phosphylation, amidation, derivatisation by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analogue or derivative may contain one or more non-classical amino acids.

The foregoing antibodies can be used in methods known in the art relating to the localisation and activity of the polypeptides used in the invention, e.g. for imaging or radio-imaging these proteins, measuring levels thereof in appropriate physiological samples, in diagnostic methods, etc. and for radiotherapy.

The antibodies of the invention can be produced by any method known in the art for the synthesis of antibodies, in particular, by chemical synthesis or by recombinant expression, and are preferably produced by recombinant expression technique.

Recombinant expression of antibodies, or fragments, derivatives or analogues thereof, requires construction of a nucleic acid that encodes the antibody. If the nucleotide sequence of the antibody is known, a nucleic acid encoding the antibody may be assembled from chemically synthesised oligonucleotides (e.g. as described in Kutmeier et al., 1994, Bio/Techniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridisable to the 3' and 5' ends of the sequence or by cloning using an oligonucleotide probe specific for the particular gene sequence.

If an antibody molecule that specifically recognises a particular antigen is not available (or a source for a cDNA library for cloning a nucleic acid encoding such an antibody), antibodies specific for a particular antigen may be generated by any method known in the art, for example, by immunising an animal, such as a rabbit, to generate polyclonal antibodies or, more preferably, by generating monoclonal antibodies. Alternatively, a clone encoding at least the Fab portion of the antibody may be obtained by screening Fab expression libraries (e.g. as described in Huse et al., 1989, Science 246:1275-1281) for clones of Fab fragments that bind the specific antigen or by screening antibody libraries (See, e.g. Clackson et al., 1991, Nature 352:624; Hane et al., 1997, Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. WO 86/05807; WO 89/01036; and U.S. Pat. No. 5,122,464). Vectors containing the complete light or heavy chain for coexpression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulphide bond with an amino acid residue that does not contain a sulphydryl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCR based methods, etc.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanised antibodies.

Once a nucleic acid encoding an antibody molecule has been obtained, the vector for the production of the antibody molecule may be produced by recombinant DNA technology using techniques well known in the art. Thus, methods for preparing the antibodies used in the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al (1990, Molecular Cloning, A Laboratory Manual, 2d Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus is an effective expression system for antibodies (Foecking et al., 1985, Gene 45:101; Cockett et al, 1990, BioTechnology 8:2).

A variety of host-expression vector systems may be utilised to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harbouring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509), and the like pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter). In mammalian host cells, a number of viral-based expression systems (e.g. an adenovirus expression system) may be utilised.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cells lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3, Academic Press, New York, 1987). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell Biol. 3:257).

The host cell may be co-transfected with two expression vectors for use within the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilising an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

In a preferred embodiment, antibodies of the invention or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and non-radioactive paramagnetic metal ions (see generally U.S. Pat. No. 4,741,900 for metal ions which can be conjugated to antibodies for use as diagnostics according to the present invention). Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Antibodies of the invention or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor. Other therapeutic moieties may include radionuclides such as $^{111}$In and 90Y; antibiotics, e.g. calicheamicin; or drugs such as but not limited to, alkylphosphocholines, topoisomerase I inhibitors, taxoids and suramin.

Techniques for conjugating such therapeutic moiety to antibodies are well known, see, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56, Alan R. Liss, Inc. 1985; Hellstrom et al., "Antibodies For Drug Delivery", in Controlled Drug Delivery, 2nd Edit., Robinson et al., eds., 1987, pp. 623-53, Marcel Dekker, Inc.; Thorpe, "Antibody Carriers Of Cytotoxic Agents In Cancer Therapy: A Review", in Monoclonal Antibodies '84: Biological And Clinical Applications; Pinchera et al. eds., 1985, pp. 475-506; "Analysis, Results, And Future Prospective Of The Therapeutic Use Of Radiolabelled Antibody In Cancer Therapy", in Monoclonal Antibodies For Cancer Detection And Therapy, Baldwin et al., eds., pp. 303-16, Academic Press 1985; Thorpe et al., 1982, Immunol. Rev., 62:119-58; and Dubowchik et al., 1999, Pharmacology and Therapeutics, 83, 67-123.

Alternatively, an antibody can be conjugated to a second antibody to form an antibody heteroconjugate as described in U.S. Pat. No. 4,676,980.

An antibody with or without a therapeutic moiety conjugated to it, can be used as a therapeutic agent that is administered alone or in combination with cytotoxic factor(s) and/or cytokine(s).

A further aspect of the invention provides methods of screening for active agents that modulate (upregulate or downregulate) a characteristic of, e.g. the expression or the enzymatic or binding activity, of a CCMP-1 polypeptide. Agents identified through the screening methods of the invention are potential therapeutics for use in the treatment of carcinoma.

The invention provides methods for identifying active agents that bind to a CCMP-1 polypeptide or have a stimulatory or inhibitory effect on the expression or activity of a CCMP-1 polypeptide. Examples of candidate agents, include, but are not limited to, nucleic acids (e.g. DNA and RNA), carbohydrates, lipids, proteins, peptides, peptidomimetics, antibodies, agonists, antagonists, small molecules and other drugs. Active agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one embodiment, agents that interact with (i.e. bind to) a CCMP-1 polypeptide are identified in a cell-based assay system. In accordance with this embodiment, cells expressing a CCMP-1 polypeptide are contacted with a candidate agent and the ability of the candidate agent to interact with the CCMP-1 polypeptide is determined. Preferably, the ability of a candidate agent to interact with a CCMP-1 polypeptide is compared to a reference range or control. In another embodiment, a first and second population of cells expressing a CCMP-1 polypeptide are contacted with a candidate agent or a control agent and the ability of the candidate agent to interact with the polypeptide is determined by comparing the difference in interaction between the candidate agent and control agent. If desired, this assay may be used to screen a plurality (e.g. a library) of candidate agents. The cell, for example, can be of prokaryotic origin (e.g. E. coli) or eukaryotic origin (e.g. yeast or mammalian). Further, the cells can express the CCMP-1 polypeptide endogenously or be genetically engineered to express the polypeptide. In some embodiments, the CCMP-1 polypeptide or the candidate agent is labelled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent. The ability of the candidate agent to interact directly or indirectly with the CCMP-1 polypeptide can be determined by methods known to those of skill in the art. For example, the interaction between a candidate agent and a polypeptide can be determined by flow cytometry, a scintillation assay, immunoprecipitation or Western blot analysis.

In another embodiment, agents that interact with (i.e. bind to) a CCMP-1 polypeptide are identified in a cell-free assay system where a native or recombinant CCMP-1 polypeptide is contacted with a candidate agent and the ability of the candidate agent to interact with the polypeptide is determined. Preferably, the ability of a candidate agent to interact with a CCMP-1 polypeptide is compared to a reference range or control. Alternatively, a first and second sample comprising native or recombinant CCMP-1 polypeptide are contacted with a candidate agent or a control agent and the ability of the candidate agent to interact with the polypeptide is determined by comparing the difference in interaction between the candidate agent and control agent. If desired, this assay may be used to screen a plurality (e.g. a library) of candidate agents. Preferably, the CCMP-1 polypeptide is first immobilized, by, for example, contacting the CCMP-1 polypeptide with an immobilized antibody which specifically recognizes and binds it, or by contacting a purified preparation of polypeptide with a surface designed to bind proteins. The CCMP-1 polypeptide may be partially or completely purified (e.g. partially or completely free of other polypeptides) or part of a cell lysate. Further, the CCMP-1 polypeptide may be a fusion protein comprising the CCMP-1 polypeptide or a biologically active portion thereof and a domain such as glutathionine-S-transferase. Alternatively, the CCMP-1 polypeptide can be biotinylated using techniques well known to those of skill in the art (e.g. biotinylation kit, Pierce Chemicals; Rockford, Ill.). The ability of a candidate agent to interact with a CCMP-1 polypeptide can be can be duplicated by methods known to those of skill in the art.

In one embodiment, a CCMP-1 polypeptide is used as a "bait protein" in a two-hybrid assay or three hybrid assay to identify other proteins that bind to or interact with the CCMP-1 polypeptide (see e.g. U.S. Pat. No. 5,283,317; Zervos et al., 1993, Cell 72:223-232; Madura et al. 1993, J. Biol. Chem. 268:12046-12054; Bartel et al., 1993, Bio/Techniques 14:920-924; Iwabuchi et al., 1993, Oncogene 8:1693-1696; and WO 94/10300). As those skilled in the art will appreciate, such binding proteins are also likely to be involved in the propagation of signals by a CCMP-1 polypeptide. For example, they may be upstream or downstream elements of a signalling pathway involving a CCMP-1 polypeptide. Alternatively, polypeptides that interact with a CCMP-1 polypeptide can be identified by isolating a protein complex comprising a CCMP-1 polypeptide (i.e. a CCMP-1 polypeptide which interacts directly or indirectly with one or more other polypeptides) and identifying the associated proteins using methods known in the art such as mass spectrometry or Western blotting (for examples see Blackstock, W. & Weir, M. 1999, Trends in Biotechnology, 17:121-127; Rigaut, G. 1999, Nature Biotechnology, 17:1030-1032; Husi, H. 2000, Nature Neurosci. 3:661-669; Ho, Y. et al, 2002, Nature, 415:180-183; Gavin, A. et al., 2002, Nature, 415: 141-147).

In all cases, the ability of the candidate agent to interact directly or indirectly with the CCMP-1 polypeptide can be determined by methods known to those of skill in the art. For example but without limitation, the interaction between a candidate agent and a CCMP-1 polypeptide can be determined by flow cytometry, a scintillation assay, an activity assay, mass spectrometry, microscopy, immunoprecipitation or Western blot analysis.

In another embodiment, agents that competitively interact with (i.e. bind to) a CCMP-1 polypeptide are identified in a competitive binding assay. In accordance with this embodiment, cells expressing the polypeptide are contacted with a candidate agent and an agent known to interact with the polypeptide; the ability of the candidate agent to competitively interact with the polypeptide is then determined. Alternatively, agents that competitively interact with (i.e. bind to) a CCMP-1 polypeptide are identified in a cell-free assay system by contacting the polypeptide with a candidate agent and an agent known to interact with the polypeptide. As stated above, the ability of the candidate agent to interact with a CCMP-1 polypeptide can be determined by methods known to those of skill in the art. These assays, whether cell-based or cell-free, can be used to screen a plurality (e.g. a library) of candidate agents.

In another embodiment, active agents that modulate (i.e. upregulate or down-regulate) the expression of a CCMP-1 polypeptide are identified in a cell-based assay. Accordingly, a population of cells expressing a CCMP-1 polypeptide or nucleic acid are contacted with a candidate agent and the ability of the candidate agent to alter expression of the CCMP-1 polypeptide or CCMP-1 nucleic acid is determined by comparison to a reference range or control. In another embodiment, a first and second population of cells expressing a CCMP-1 polypeptide or CCMP-1 nucleic acid are contacted with a candidate agent or a control agent and the ability of the candidate agent to alter the expression of the CCMP-1 polypeptide or CCMP-1 nucleic acid is determined by comparing the difference in the level of expression of the CCMP-1 polypeptide or CCMP-1 nucleic acid between the first and second populations of cells. In a further embodiment, the expression of the CCMP-1 polypeptide or CCMP-1 nucleic acid in the first population may be further compared to a reference range or control. The candidate agent can then be identified as a modulator of the expression of the CCMP-1 polypeptide or nucleic acid based on this comparison. For example, when expression of the CCMP-1 polypeptide or mRNA encoding said polypeptide is significantly greater in the presence of the candidate agent than in its absence, the candidate agent is identified as a stimulator of expression of the CCMP-1 polypeptide or mRNA encoding said polypeptide. Alternatively, when expression of the CCMP-1 polypeptide or mRNA encoding the polypeptide is significantly less in the presence of the candidate agent than in its absence, the candidate agent is identified as an inhibitor of the expression of the CCMP-1 polypeptide or mRNA encoding the polypeptide. The level of expression of a CCMP-1 polypeptide, or the mRNA that encodes it, can be determined by methods known to those of skill in the art based on the present description. For example, CCMP-1 mRNA expression can be assessed by Northern blot analysis or RT-PCR, and protein levels can be assessed by Western blot analysis or other means known in the art.

In another embodiment, active agents that modulate the activity of a CCMP-1 polypeptide are identified by contacting a preparation containing the CCMP-1 polypeptide, or cells (e.g. prokaryotic or eukaryotic cells) expressing the CCMP-1 polypeptide with a candidate agent or a control agent and determining the ability of the candidate agent to modulate (e.g. stimulate or inhibit) the activity of the CCMP-1 polypeptide. The activity of a CCMP-1 polypeptide can be assessed by detecting its effect on a "downstream effector" for example, but without limitation, induction of a cellular signal transduction pathway of the polypeptide (e.g. intracellular $Ca^{2+}$, diacylglycerol, $IP_3$, cAMP, or other intermediate), detecting catalytic or enzymatic activity of the CCMP-1 polypeptide on a suitable substrate, detecting the induction of a reporter gene (e.g. a regulatory element that is responsive to a CCMP-1 polypeptide and is operably linked to a nucleic acid encoding a detectable marker, e.g. luciferase), or detecting a cellular response, for example, cellular differentiation, or cell proliferation as the case may be, based on the present description, techniques known to those of skill in the art can be used for measuring these activities (see, e.g. U.S. Pat. No. 5,401,639). The candidate agent can then be identified as a modulator of the activity of a CCMP-1 polypeptide by comparing the effects of the candidate agent to the control agent. Suitable control agents include PBS and normal saline (NS).

In another embodiment, a cell-based assay system is used to identify active agents that bind to or modulate the activity of a protein, such as an enzyme, or a biologically active portion thereof, which is responsible for the production or degradation of the CCMP-1 polypeptide or is responsible for the post-translational modification of the CCMP-1 polypeptide. In a primary screen, a plurality (e.g. a library) of agents are contacted with cells that naturally or recombinantly express: (i) a CCMP-1 polypeptide; and (ii) a protein that is responsible for processing of the CCMP-1 polypeptide in order to identify compounds that modulate the production, degradation, or post-translational modification of said CCMP-1 polypeptide. If desired, active agents identified in the primary screen can then be assayed in a secondary screen against cells naturally or recombinantly expressing the CCMP-1 polypeptide. The ability of the candidate agent to modulate the production, degradation or post-translational modification of a CCMP-1 polypeptide can be determined by methods known to those of skill in the art, including without limitation, a kinase assay, a phosphatase assay, flow cytometry, a scintillation assay, immunoprecipitation and Western blot analysis.

In yet another embodiment, cells expressing a CCMP-1 polypeptide are contacted with a plurality of candidate agents. The ability of such an agent to modulate the production, degradation or post-translational modification of a CCMP-1 polypeptide can be determined by methods known to those of skill in the art, as described above.

In another embodiment, active agents that modulate (i.e. upregulate or down-regulate) the expression, activity or both the expression and activity of a CCMP-1 polypeptide are identified in an animal model. Examples of suitable animals include, but are not limited to, mice, rats, rabbits, monkeys, guinea pigs, dogs and cats. Preferably, the animal used represents a model of carcinoma. Accordingly, a first and second group of mammals are administered with a candidate agent or a control agent and the ability of the candidate agent to modulate the expression of the CCMP-1 polypeptide or nucleic acid is determined by comparing the difference in the level of expression between the first and second group of mammals. Where desired, the expression levels of the CCMP-1 polypeptide or nucleic acid in the first and second groups of mammals can be compared to the level of a CCMP-1 polypeptide or nucleic acid in a control group of mammals. The candidate agent or a control agent can be administered by means known in the art (e.g. orally, rectally or parenterally such as intraperitoneally or intravenously). Changes in the expression of a CCMP-1 polypeptide or nucleic acid can be assessed by the methods outlined above. In a particular embodiment, a thera-peutically effective amount of an agent can be determined by monitoring an amelioration or improvement in disease symptoms, to delay onset or slow progression of the disease, for example but without limitation, a reduction in tumour size. Techniques known to physicians familiar with carcinoma can be used to determine whether a candidate agent has altered one or more symptoms associated with the disease.

The present invention also provides assays for use in drug discovery in order to identify or verify the efficacy of compounds for treatment or prevention of carcinoma. Test compounds can be assayed for their ability to modulate levels of a CCMP-1 polypeptide in a subject having carcinoma. Compounds able to modulate levels of a CCMP-1 polypeptide in a subject having carcinoma towards levels found in subjects free from carcinoma or to produce similar changes in experimental animal models of carcinoma can be used as lead compounds for further drug discovery, or used therapeutically. Such assays can also be used to screen candidate drugs, in clinical monitoring or in drug development, where abundance of a CCMP-1 polypeptide can serve as a surrogate marker for clinical disease.

One skilled in the art will also appreciate that a CCMP-1 polypeptide may also be used in a method for the structure-based design of an agent, in particular a small molecule which acts to modulate (e.g. stimulate or inhibit) the activity of said polypeptide, said method comprising:
1) determining the three-dimensional structure of said polypeptide;
2) deducing the three-dimensional structure within the polypeptide of the likely reactive or binding site(s) of the agent;
3) synthesising candidate agents that are predicted to react or bind to the deduced reactive or binding site; and
4) testing whether the candidate agent is able to modulate the activity of said polypeptide.

It will be appreciated that the method described above is likely to be an iterative process.

This invention further provides agents identified by the above-described screening assays, CCMP-1 polypeptides and CCMP-1 nucleic acids and uses thereof for treatments as described herein. Hereinafter, the agents, CCMP-1 polypeptides, antibodies thereto and CCMP-1 nucleic acids of use in treatment are referred to as 'active agents'. The term 'treatment' includes either therapeutic or prophylactic therapy. When a reference is made herein to a method of treating or preventing a disease or condition using a particular active agent or combination of agents, it is to be understood that such a reference is intended to include the use of that active agent or combination of agents in the preparation of a medicament for the treatment or prevention of the disease or condition.

Accordingly, the present invention provides a method for the prophylaxis and/or treatment of carcinoma, which comprises administering to said subject a therapeutically effective amount of at least one active agent of the invention.

In yet another aspect, the present provides a pharmaceutical composition comprising at least one active agent of the invention, optionally together with one or more pharmaceutically acceptable excipients, carriers or diluents.

In one embodiment, one or more active agents are administered alone or in combination with one or more additional treatments or therapeutic compounds for carcinoma. Examples of such treatments include, surgery and radiation therapy. Examples of therapeutic compounds include but are not limited to cyclophosphamide (Cytoxan™); methotrexate (Methotrexate™); 5-fluorouracil (5-FU); paclitaxel (Taxol); docetaxel (Taxotere™); vincristine (Oncovin™); vinblastine (Velban™); vinorelbine (Navelbine™); doxorubicin (Adriamycin); tamoxifen (Nolvadex™); toremifene (Fareston™); megestrol acetate (Megace™); anastrozole (Arimidex™); goserelin (Zoladex™); anti-HER2 monoclonal antibody (Herceptin™); capecitabine (Xeloda™) and raloxifene hydrochloride (Evista™).

In order to use active agents of the invention in therapy (human or veterinary), they will normally be formulated into a pharmaceutical composition in accordance with standard pharmaceutical practice, e.g. by admixing the active agent and a pharmaceutically acceptable carrier. Thus, according to a further aspect of the invention there is provided a pharmaceutical composition comprising at least one active agent of the invention and a pharmaceutically acceptable carrier. The pharmaceutical compositions are particularly useful in the prevention or treatment of carcinoma. In one aspect, the pharmaceutical composition is for use as a vaccine and so any additional components will be acceptable for vaccine use. In addition, the skilled person will appreciate that one or more suitable adjuvants may be added to such vaccine preparations.

Active agents of the invention may be administered to a subject by any of the routes conventionally used for drug administration, for example they may be administered parenterally, orally, topically (including buccal, sublingual or transdermal) or by inhalation. The most suitable route for administration in any given case will depend on the particular active agent, the carcinoma involved, the subject, and the nature and severity of the disease and the physical condition of the subject.

The active agents may be administered in combination, e.g. simultaneously, sequentially or separately, with one or more other therapeutically active, e.g. anti-tumour, compounds.

The dosage to be administered of an active agent will vary according to the particular active agent, the carcinoma involved, the subject, and the nature and severity of the disease and the physical condition of the subject, and the selected route of administration; the appropriate dosage can be readily determined by a person skilled in the art. For the treatment of carcinoma and tumours in humans and animals, the dosage may range from 0.01 mg/kg to 750 mg/kg. For prophylactic use in human and animals, the dosage may range from 0.01 mg/kg to 100 mg/kg.

The compositions may contain from 0.1% by weight, preferably from 10-60% by weight, of the active agent of the invention, depending on the method of administration.

Pharmaceutical compositions may be conveniently presented in unit dose forms containing a predetermined amount of an active agent of the invention per dose. Such a unit may contain for example but without limitation, 750 mg/kg to 0.01 mg/kg depending on the condition being treated, the route of administration and the age, weight and condition of the subject. Preferred unit dosage compositions are those containing a daily dose or sub-dose, as recited above, or an appropriate fraction thereof, of the active agent.

It will be recognized by one of skill in the art that the optimal quantity and spacing of individual dosages of an active agent of the invention will be determined by the nature and extent of the condition being treated, the form, route and site of administration, and the particular subject being treated, and that such optimums can be determined by conventional techniques. It will also be appreciated by one of skill in the art that the optimal course of treatment, i.e. the number of doses of an active agent of the invention given per day for a defined number of days, can be ascertained by those skilled in the art using conventional course of treatment determination tests.

Dosage regimens are adjusted to provide the optimum desired response. For example, a single bolus may be administered, several divided doses may be administered over time or the dose may be proportionally reduced or increased as indicated by the exigencies of the therapeutic situation.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; water; non-aqueous vehicles (which may include edible oils), for example almond oil, oily esters such as glycerine, propylene glycol, or ethyl alcohol; preservatives, for example methyl or propyl p-hydroxybenzoate or sorbic acid; flavoring agents, preservatives, coloring agents and the like may be used.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Compressed tablets may be prepared by compressing, in a suitable machine, the active agent in a free-flowing form such as a powder or granules, optionally mixed with a binder, lubricant, inert diluent, surface active or dispersing agent. Moulded tablets may be made by moulding, in a suitable machine, a mixture of the powdered compound moistened with an inert liquid diluent. Desirably, each tablet contains from about 1 mg to about 500 mg of the active agent and each cachet or capsule contains from about 1 to about 500 mg of the active agent.

Compositions comprising an active agent of the invention may also be prepared in powder or liquid concentrate form. Conventional water soluble excipients, such as lactose or sucrose, may be incorporated in the powders to improve their physical properties. Thus, particularly suitable powders of this invention comprise 50 to 100% w/w, and preferably 60 to 80% w/w of the combination and 0 to 50% w/w and preferably 20 to 40% w/w of conventional excipients. When used in a veterinary setting such powders may be added to animal feedstuffs, for example by way of an intermediate premix, or diluted in animal drinking water.

Liquid concentrates of this invention for oral administration suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

The compositions may be presented in unit-dose or multi-dose containers, for example in sealed ampoules and vials and to enhance stability, may be stored in a freeze-dried (lyophilized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included the sterile liquid carrier.

In certain embodiments, the active agents of the invention can be formulated to ensure proper distribution in vivo, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g. Ranade, V. 1989, J. Clin. Pharmacol. 29: 685).

Exemplary targeting moieties include folate or biotin (see, e.g., U.S. Pat. No. 5,416,016); mannosides (Umezawa et al., 1988, Biochem. Biophys. Res. Comm. 153:1038); antibodies (Bloeman, P. et al., 1995, FEBS Lett. 357:140; Owais, M. et al. (1995) Antimicrob. Agents Chemother. 39: 180); surfactant protein A receptor (Briscoe et al. (1995) Am. J. Physiol. 1233: 134), different species of which may comprise the compositions of the inventions, as well as components of the invented molecules; psi 20 (Schreier et al. (1994) J. Biol. Chem. 269: 9090); see also Keinanen, K. & Laukkanen, M., 1994, FEBS Lett. 346: 123; Killion, J. & Fidler, I., 1994, Immunomethods 4: 273. In one embodiment of the invention, the active agents of the invention are formulated in liposomes; in a more preferred embodiment, the liposomes include a targeting moiety. In a most preferred embodiment, the therapeutic compounds in the liposomes are delivered by bolus injection to a site proximal to the tumour.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

Pharmaceutical compositions adapted for vaginal administration may be presented as pessaries, tampons, creams, gels, pastes, foams or spray compositions. These may comprise emollients or bases as commonly used in the art.

In view of the importance of CCMP-1 in carcinoma, the following form additional aspects of the present invention:

i) a method of screening for compounds that modulate, e.g. up-regulate or down-regulate, the expression of a CCMP-1 polypeptide.

ii) a method for monitoring/assessing carcinoma treatment in a patient, which comprises the step of determining the presence or absence and/or quantifying a CCMP-1 polypeptide in a biological sample obtained from said patient;

iii) a method for the identification of carcinoma cells in a biological sample obtained from a subject, which comprises the step of determining the presence or absence and/or quantifying at least one CCMP-1 polypeptide;

(iv) methods of treating carcinoma, comprising administering to a patient a therapeutically effective amount of an active agent that modulates (e.g. upregulates or downregulates) or complements the expression or the biological activity (or both), or interaction of a CCMP polypeptide or CCMP-1 nucleic acid in patients having carcinoma, (v) the use of a CCMP-1 polypeptide or CCMP-1 nucleic acid in the manufacture of a medicament in order to (a) prevent the onset or development of carcinoma; (b) prevent the progression of carcinoma; or (c) ameliorate the symptoms of carcinoma.

(vi) the use of an antibody that recognises a CCMP-1 polypeptide in the manufacture of a medicament for the treatment of carcinoma;

(vii) the use of an antibody conjugated to a therapeutic moiety, said antibody recognising a CCMP-1 polypeptide, in the manufacture of a medicament for the treatment of carcinoma;

(viii) a method of treatment of carcinoma in a subject, which comprises administering to said subject a therapeutically effective amount of an antibody recognising a CCMP-1 polypeptide;

(ix) an antibody recognising a CCMP-1 polypeptide for use in the treatment of carcinoma;

(x) a method of treatment of carcinoma in a subject, which comprises administering to said subject a therapeutically effective amount of an agent which interacts with or modulates the expression or activity of a CCMP-1 polypeptide or CCMP-1 nucleic acid; and (xi) an agent which interacts with or modulates the expression or activity of a CCMP-1 polypeptide or CCMP-1 nucleic acid for use in the treatment of carcinoma.

Preferred features of each aspect of the invention are as for each of the other aspects mutatis mutandis. The documents including patents and patent applications mentioned herein are incorporated to the fullest extent permitted by law.

DESCRIPTION OF THE FIGURES

FIG. 1 shows the nucleotide and predicted amino acid sequences of CCMP-1 (SEQ ID NO: 2 and SEQ ID NO: 1, respectively). The tandem mass spectrum is in bold and is underlined.

EXAMPLE 1

Figure 2:
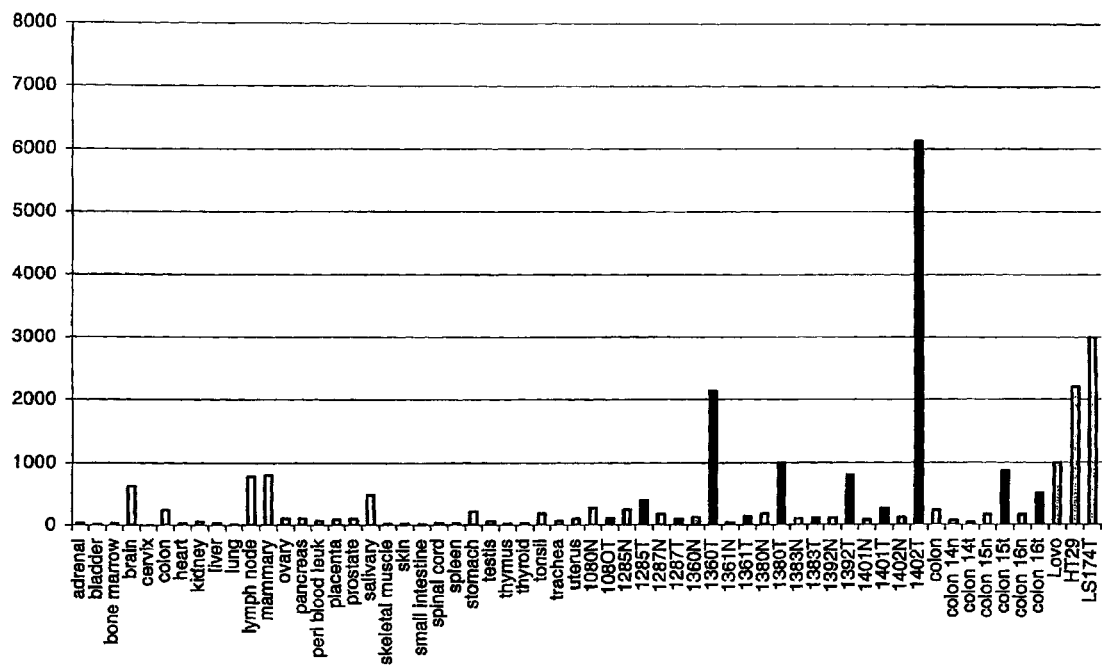
FIG. 2 shows tissue distribution of CCMP-1 mRNA. Levels of mRNA in normal tissues (open bars) and normal colon tissues (spotted bars), colon adenocarcinoma tissues (solid bars) and colon carcinoma cell lines (hatched bars) were quantified by real time RT-PCR. mRNA levels are expressed along the y-axis as the number of copies $ng^{-1}$ cDNA.

Identification of CCMP-1 in Colon Adenocarcinoma Cell Lines

CCMP-1 was isolated from colorectal cancer cell membranes and breast cancer cell membranes, purified by 1D gel electrophoresis and characterised by mass spectrometry before being cloned.

Proteins in colon adenocarcinoma cell line membranes were separated by SDS-PAGE and analysed.

Crude Fractionation of Adherent Colon Adenocarcinoma Cell Lines

1a—Cell Culture

Cell lines LoVo (ECACC 87060101) and LS174T (ECACC 87060401) were cultured in Hams F12 or EMEM plus 1% NEM media respectively, supplemented with 10% foetal calf serum, 2 mM glutamine, 1% penicillin and 1% streptomycin. The cells were grown at 37° C. in a humidified atmosphere of 95% air and 5% carbon dioxide.

1b—Cell Fractionation and Plasma Membrane Generation

Purified membrane preparations were isolated from a pool of colon adenocarcinoma cell lines. Adherent cells ($2 \times 10^8$) were washed three times with PBS and scraped using a plastic cell lifter. Cells were centrifuged at 1000×g for 5 min at 4° C. and the cell pellet was resuspended in homogenization buffer (250 mM Sucrose, 10 mM HEPES, 1 mM EDTA, 1 mM Vanadate and 0.02% azide, protease inhibitors). Cells were fractionated using a ball bearing homogeniser (8.002 mm ball, HGM Lab equipment) until approx. 95% of cells were broken. Membranes were fractionated using the method described by Pasquali et al. The fractionated cells were centrifuged at 3000×g for 10 min at 4° C. and the postnuclear supernatant was layered onto a 60% sucrose cushion and centrifuged at 100 000×g for 45 min. The membranes were collected using a pasteur pipette and layered on a preformed 15 to 60% sucrose gradient and spun at 100 000×g for 17 hr. Proteins from the fractionated sucrose gradient were run on a 4-20% 1D gel (Novex) and subject to western blotting; those fractions containing alkaline phosphatase and transferrin immunoreactivity but not oxidoreductase II or calnexin immunoreactivity were pooled and represented the plasma membrane fraction.

1c—Preparation of Plasma Membrane Fractions for 1D-Gel Analysis

Plasma membrane fractions were pooled and diluted at least four times with 10 mM HEPES, 1 mM EDTA 1 mM Vanadate, 0.02% Azide. The diluted sucrose fraction was added to a SW40 or SW60 tube and centrifuged at 100 000×g for 45 min with slow acceleration and deceleration. The supernatant was removed from the membrane pellet and the pellet washed three times with PBS-CM. The membrane pellet was solubulized in 2% SDS in 63 mM Tris HCl, pH 7.4. A protein assay was performed followed by the addition of mercaptoethanol (2% final), glycerol (10%) and bromophenol blue (0.0025% final) was added. A final protein concentration of 1 microgram/microlitre was used for 1D-gel loading.

1d-1D—Gel Technology

Protein or membrane pellets were solubilised in 1D-sample buffer (approximately 1 mg/ml) and the mixture heated to 95° C. for 5 min.

Samples were separated using 1D-gel electrophoresis on pre-cast 8-16% gradient gels purchased from Bio-Rad (Bio-Rad Laboratories, Hemel Hempstead, UK). A sample containing 30-50 micrograms of the protein mixtures obtained from a detergent extract were applied to the stacking gel wells using a micro-pipette. A well containing molecular weight (10, 15, 25, 37, 50, 75, 100, 150 and 250 kDa) was included for calibration by interpolation of the separating gel after imaging. Separation of the proteins was performed by applying a current of 30 mA to the gel for approximately 5 hr or until the bromophenol blue marker dye had reached the bottom of the gel.

After electrophoresis the gel plates were prised open, the gel placed in a tray of fixer (10% acetic acid, 40% ethanol, 50% water) and shaken overnight. The gel was then primed for 30 min by shaking in a primer solution (7.5% acetic acid, 0.05% SDS in Milli-Q water) followed by incubation with a fluorescent dye (0.06% OGS dye in 7.5% acetic acid) with shaking for 3 hr. A preferred fluorescent dye is disclosed in U.S. Pat. No. 6,335,446. Sypro Red (Molecular Probes, Inc., Eugene, Oreg.) is a suitable alternative dye for this purpose.

A digital image of the stained gel was obtained by scanning on a Storm Scanner (Molecular Dynamics Inc, USA) in the blue fluorescence mode. The captured image was used to determine the area of the gel to excise for in-gel proteolysis.

1e—Recovery and Analysis of Selected Proteins

Each vertical lane of the gel was excised using either a stainless steel scalpel blade or a PEEK gel cutter (OGS) that cuts sequentially down the length of the gel lane with no attempt at collecting specific protein bands. The protein CCMP-1 had an apparent MW of 17.9 kDa.

Proteins were processed using in-gel digestion with trypsin (Modified trypsin, Promega, Wisconsin, USA) to generate tryptic digest peptides. Recovered samples were divided into two. Prior to MALDI analysis samples were desalted and concentrated using Cl 8 Zip Tips™ (Millipore, Bedford, Mass.). Samples for tandem mass spectrometry were purified using a nano LC system (LC Packings, Amsterdam, The Netherlands) incorporating C 18 SPE material. Recovered peptide pools were analysed by MALDI-TOF-mass spectrometry (Voyager STR, Applied Biosystems, Framingham, Mass.) using a 337 nm wavelength laser for desorption and the reflectron mode of analysis. Pools were also analyzed by nano-LC tandem mass spectrometry (LC/MS/MS) using a Micromass Quadrupole Time-of-Flight (Q-TOF) mass spectrometer (Micromass, Altrincham, UK). For partial amino acid sequencing and identification of colon carcinoma membrane proteins uninterpreted tandem mass spectra of tryptic peptides were searched against a database of public domain proteins constructed of protein entries in the non-redundant database held by the National Centre for Biotechnology Information (NCBI) which is accessible at http://www.ncbi.nim.nih.gov/using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art (in the case of interpretation of low-energy fragmentation mass spectra of peptide ions see Gaskell et al., 1992, Rapid Commun. Mass Spectrom. 6:658-662). The method described in WO 02/21139 was also used to interpret mass spectra.

One tandem spectrum (see FIG. 1) and mass 1672.9 Da was found to match GenBank Accession No. X75208.1 and SwissProt Accession No. P54753 which correspond to CCMP-1.

EXAMPLE 2

Expression of CCMP-1 mRNA in Human Tissues

Real time quantitative RT-PCR (Heid, et al., 1996, Genome Res. 6: 986-994; Morrison, et al, 1988, Bio/Techniques 24: 954-958) was used to analyse the distribution of CCMP-1 mRNA in normal colon and colon tumour tissues and adenocarcinoma cell lines (see FIG. 2) and normal breast tissue removed during breast reduction mammoplasty and breast cancer tissues removed during surgery and mammary carcinoma cell lines (see FIG. 3). Ethical approval for the normal and tumour breast samples was obtained at surgery (University of Oxford, UK). The primers used for PCR were as follows: sense, 5' actgatcctcgagtggagtgag 3' (SEQ ID NO:3), antisense, 5' cacctcaaaggtgtagcgcgtg 3' (SEQ ID NO:4). Reactions containing 10 ng cDNA, prepared as described above, SYBR green sequence detection reagents (PE Biosystems) and sense and antisense primers were assayed on an ABI7700 sequence detection system (PE Biosystems). The PCR conditions were 1 cycle at 50° C. for 2 min, 1 cycle at 95° C. for 10 min, and 40 cycles of 95° C. for 15 s/65° C. for 1 min. The accumulation of PCR product was measured in real time as the increase in SYBR green fluorescence, and the data were analysed using the Sequence Detector program v1.6.3 (PE Biosystems). Standard curves relating initial template copy number to fluorescence and amplification cycle were generated using the amplified PCR product as a template, and were used to calculate CCMP-1 copy number in each sample.

Expression of CCMP-1 in human tissue showed that the highest levels of expression were found in mammary gland, brain, salivary gland and lymph node. CCMP-1 mRNA was also detected in the prostate cancer cell lines PC3 and PC3M: expression in PC3 cells was elevated in comparison to normal prostate (not shown). Little or no CCMP-1 mRNA was detected in the other cell lines or normal tissues examined. The highest levels of CCMP-1 expression were observed in the colon carcinoma cell line LS174T (3000 copies ng$^{-1}$ cDNA; FIG. 2), with lower levels of expression in the LoVo cell line (1000-1100 copies ng$^{-1}$ cDNA; FIG. 2). CCMP-1 mRNA was also detected in mammary carcinoma cell lines BT-20 (ATCC HTB-19), BT-474 (HTB-20), MCF-7 (ATCC HTB-22; ECACC 86012803), T47D, MDA-MB-468 (ATCC HTB-132) and MDA-MB-453 (ATCC HTB-131) with a range of 500-4400 copies ng$^{-1}$ cDNA (see FIG. 3).

Figure 3:
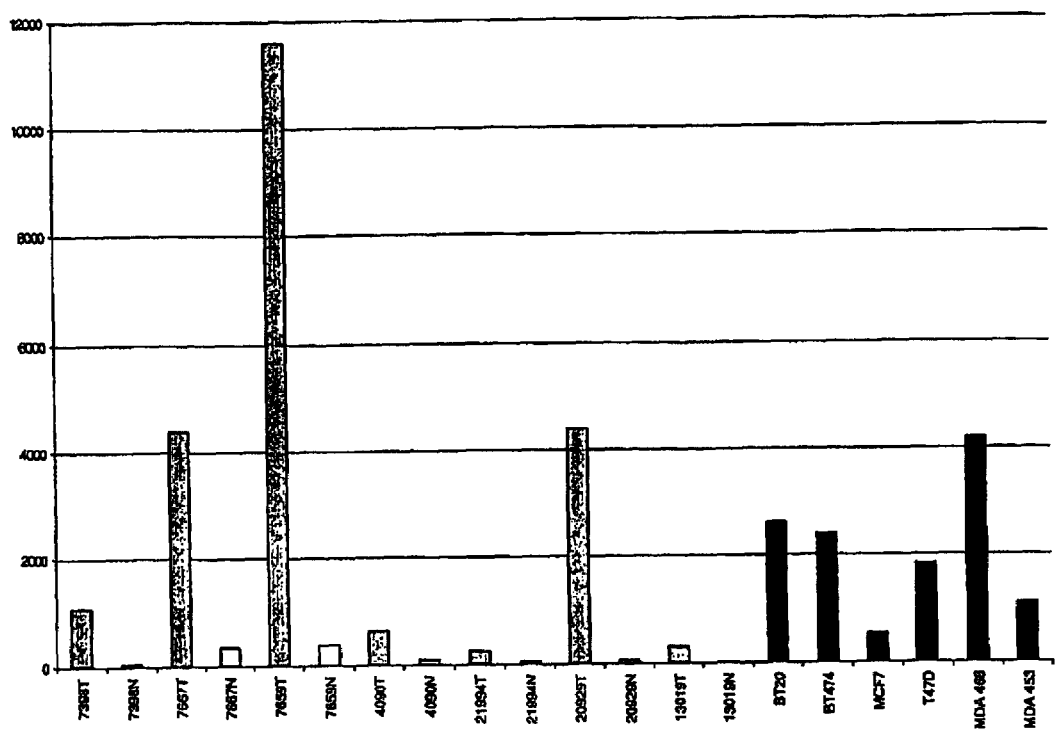
FIG. 3 shows the expression of CCMP-1 in normal breast tissues (open bars), tumour breast tissues (hatched bars) and breast cancer cell lines (solid bars). Levels of CCMP-1 mRNA in matched normal and tumour tissues from seven breast cancer patients were measured by real time RT-PCR. mRNA levels are expressed as the number of copies $ng^{-1}$ cDNA.

To examine whether the observed elevation in CCMP-1 expression in some colon and breast carcinoma lines is reiterated in clinical samples, the expression of mRNA in matched normal and tumour tissue samples from thirteen colon cancer patients was also measured (FIG. 2; samples 1080 through 1402 and 14 through 16, where N normal tissue and T=tumour tissue) and seven breast cancer patients (FIG. 3, where N=normal tissue and T=tumour tissue). CCMP-1 expression was increased in nine of the colon tumour samples, relative to their matched normal tissues: increases in expression levels ranged from approximately 1.6- to 16-fold (FIG. 2) and in all seven breast tumour samples and breast cell lines (FIG. 3). Note the different y-axis scales between FIGS. 2 and 3.

Thus, CCMP-1 shows a restricted pattern of expression in normal human tissues, and is elevated in some colon and breast tumours, suggesting that this protein a potential therapeutic target.

EXAMPLE 3

Cloning and Expression of CCMP-1

Full length CCMP-1 was amplified from a pool of cDNAs (colon, HT29 cells, mammary, LS174T cells) using forward primer: ctcggctcctagagctgcc (SEQ ID NO:5); reverse primer: ctgcttggcatccctgcac (SEQ ID NO:6) and the following PCR conditions: 94° C. for 3 min -1 cycle; 94° C. for 30 s, 55° C. for 30 s, 72° C. for 3 min-40 cycles and 72° C. for 3 min-1 cycle. The PCR product was amplified with Stratagene Pfu enzyme. The PCR product coding for CCMP-1 was initially cloned into pCR4 (Invitrogen) and then re-amplified and cloned into pcDNA3.1 (Invitrogen) with a C-terminal V5-hexaHIS tag at KpnI/BamHI sites.

CCMP-1 cloned into pcDNA3.1 neomycin vector (Invitrogen) was transfected into HEK 293 cells (GeneJuice, Novagen). The cells were selected in 0.8 mg/ml Geneticin (antibiotic G418, Sigma) and resistant cells were pooled and used as a mixed clone pool. HEK 293 cells (primary human embryo kidney cells, ATCC no: CRL-1537) were grown in Dulbecco's medium NUT mix F12, 10% Fetal Calf serum, 2 mM glutamine.

A polyclonal antibody was raised against CCMP-1 using the services of Abcam Ltd., Cambridge, UK. The antibody was raised in rabbits immunized with two specific peptides whose sequences were chosen for synthesis based on plots of hydrophobicity, antigenicity, surface probability, and low identity to other known protein family members. Peptides were synthesized using Fmoc chemistry with a cysteine residue added to the end to enable specific thiol reactive coupling of Keyhole limpet Hemocyanin prior to immunization. The CCMP-1 peptides used were: GQYSRPAEFETTSER (SEQ ID NO:7) and CATGHEPAAKESQ (SEQ ID NO:8).

Western blotting with the antisera raised recognized a band of approximately 110 kDa in HEK 293 cell lysate from the mixed clone pool which over-expressed CCMP-1 but not the parental HEK 293 cells. This recombinant protein also expressed a V5 tag which is recognized by a specific monoclonal antibody (Invitrogen). Western Blotting with the anti-V5 tag antibody also recognized a single band of approximately 110 kDa in HEK 293 cell lysate expressing CCMP-1.

These antisera also recognized a protein of identical molecular weight in LS174T cell lysates (human colon adenocarcinoma, adherent, ATCC CL-188).

Measurement of Tyrosine Phosphorylation of CCMP-1

Parental HEK 293 cells and HEK 293 cells over-expressing recombinant CCMP-1 with a V5 tag were grown as described above. Cells were treated for various times in the presence or absence of 500 ng/ml recombinant LERK8-Fc chimera protein (also known as Ephrin B3 which is a ligand for CCMP-1; R&D Sytems). LERK8-Fc is a soluble ligand comprising the extracellular domain of LERK8 fused to the Fc region of a human IgG molecule via a polypeptide linker; this permits the LERK8-Fc protein to be detected using standard anti-human secondary antibodies. Cells were harvested and lysed in buffer (20 mM-Tris HCL pH 7.6, 1 mM-EDTA, 150 mM-NaCl, 10 mM-NaF, 1 mM-sodium orthovanadate), mixed and left on ice for 20 min. The cell lysate was then spun at 10,000×g and the supernatant separated by 1D-SDS PAGE electrophoresis. The cell lysate was then subjected to Western Blotting using RC20 anti-phosphotyrosine antibody (Transduction laboratories).

It was found that HEK 293 cells over-expressing CCMP-1 showed increased phosphorylation upon treatment with the LERK8 ligand (500 ng/ml) compared to untreated cells grown in serum or in serum free conditions. Tyrosine phosphorylation was highest between 30 min and 2 hr, but remained increased at 6 hr and 24 hr compared to untreated cells. LERK8 treatment also resulted in a decrease in CCMP-1 protein levels as seen by Western blotting using an anti-V5 antibody. Western blots were also stained with Ponceau S and showed that LERK8 treated cells had equivalent protein loadings to the untreated cells.

Phosphotyrosine Immunoprecipitation in LS174T Cells

To demonstrate CCMP-1 phosphorylation in LS174T cells which express endogenous CCMP-1, lysates were prepared as described above, from cells which were treated with LERK8 ligand (500 ng/ml). Lysates were incubated for 1 hr at 4° C. with 10 µl of PY-20H anti-phosphotyrosine antiserum (Transduction laboratories). The antibody was then captured using protein A Sepharose beads (Pierce). The beads were washed three times with PBS and bound protein eluted by the addition of 20 µl of 1D-SDS-PAGE sample buffer lysis buffer. The immunoprecipitate was separated by 1D-SDS-PAGE electrophoresis and subjected to Western blotting using anti-CCMP-1 antisera. These data indicated that LERK8 ligand treatment resulted in an increase in tyrosine phosphorylation in LS174T cells from 10 min to 2 hr.

EXAMPLE 4

Immunocytochemical Analysis of HEK 293 Cells Expressing Recombinant CCMP-1

Parental HEK 293 cells and HEK 293 cells over-expressing recombinant CCMP-1 with a V5 tag were plated overnight, fixed in 4% paraformaldehyde/PBS and then blocked and permeabilised by incubation in 10% Donkey Serum/0.3% Triton X-100/PBS for one hr. To detect CCMP-1 via the C-terminal V5 tag, cells were probed using 1:500 anti-V5 antibody (invitrogen) in 2.5% donkey serum/0.075% Triton X-100/PBS, washed 3 times in PBS then incubated for another hour in biotinylated anti-mouse secondary antibody (Jackson Laboratories) in 2.5% donkey serum/0.075% Triton X-100/PBS. To detect CCMP-1 using the binding properties of CCMP-1 for its ligand, LERK8, cells were incubated in 500 ng/ml LERK8-Fc in 2.5% donkey serum/0.075% Triton X-100/PBS, washed 3 times in PBS then incubated for a further 1 hr in biotinylated anti-human secondary antibody (Jackson Laboratories). Cells were then washed 3 times in PBS then incubated with Extravadin Cy-3 (Sigma).

Immunocytochemical staining using anti-V5 tag antibody clearly demonstrated the localisation of recombinant CCMP-1 protein to the cell membrane of the transfected HEK 293 cells. In these transfected cells the staining was most intense at sites of cell-cell contact and on the outer membrane of the cell with no obvious nuclear, perinuclear or cytosolic staining. No staining in the parental HEK 293 cells indicated that the antibody was binding specifically to the tagged recombinant protein in the transfected cells. Using the LERK-Fc ligand as a probe similar staining patterns were seen in the transfected HEK 293 cells, with minimal background in the non-transfected cells.

Taken together, these results demonstrate that i) recombinant CCMP-1 is expressed and localised to the cell membrane; and ii) the recombinant CCMP-1 is folded properly, in that it can bind to LERK8; and iii) LERK8-Fc can be used to follow CCMP-1 localisation.

EXAMPLE 5

LERK8 Binding to CCMP-1 Induces CCMP-1 Internalisation

CCMP-1 transfected HEK 293 cells were plated overnight and incubated under standard tissue culture conditions in the presence or absence of 500 ng/ml LERK8-Fc ligand for 2 hr prior to fixation in paraformaldehyde/PBS. Cells were blocked and permeabilised by incubation in 10% Donkey Serum/0.3% Triton X-100/PBS for an hour before sequential incubation in 500 ng/ml LERK8-Fc (R & D systems), then biotinylated anti-human secondary antibody (Jackson Laboratories) and finally Extravadin Cy-3 (Sigma) all diluted in 2.5% donkey serum/0.075% Triton X-100/PBS and with three washes in PBS in between each incubation.

CCMP-1 in untreated CCMP-1 transfected HEK 293 cells was localised to the cell membrane. The localisation of CCMP-1 in the HEK 293 cells is most intense at the end of lamellipodia. In LERK8 treated HEK 293 cells, two hours of incubation with LERK-8 Fc resulted in the loss of essentially all of the cell membrane staining. Intense, granular cytoplasmic staining was instead present, indicative of internalisation.

Flow Cytometry

CCMP-1 transfected HEK 293 cells and LS174T cells were plated overnight and incubated under standard tissue culture conditions in the presence or absence of 500 ng/ml LERK8-Fc ligand for 10 min, 2 hr or 24 hr, respectively. Cells were dissociated from the tissue culture plate and 500,000 cells per condition transferred into a 96 well plate for subsequent processing at 4° C. After washing (by spinning and then re-suspension) in flow buffer (1% BSA/0.1% azide/PBS) cells were incubated in 500 ng/ml LERK8-Fc in the same buffer for 30 min. Cells were washed 3 times in flow buffer and then incubated in phycoerythrin (PE) conjugated anti-human secondary antibody (AbCam, cat no 7006) diluted 1:50 in flow buffer for 30 min in the dark. After 1 wash in flow buffer and 2 washes in Isoton Flow Cytometry Solution (Beckman Coulter) the mean fluorescence of a pool of cells was obtained by analysis using a Beckman Coulter Epics XL.MCL Flow Cytometer.

The addition of LERK8 to the HEK 293 cells in culture resulted in a rapid decrease in the mean cell fluorescence consistent with internalisation of the CCMP-1 protein. The drop in mean cell fluorescence caused by incubation with LERK8 that is seen in LS174T cells indicates that these cell also express CCMP-1 on the cell membrane and hence that endogenous CCMP-1 is expressed on the surface of human derived carcinoma cell lines. A decrease in mean cell fluorescence was also seen in LS174T cells when taken in conjunction with the immunocytochemistry results is consistent with internalisation of the endogenous CCMP-1 in these cells.

The above findings suggests that antibody binding to CCMP-1 may result in internalisation of the antibody which may include an antibody which is conjugated to a toxin, cytokine or radionucleotide. Thus CCMP-1 represents a good target for immunotherapy-based approaches to the treatment of carcinoma.

EXAMPLE 6

LERK8 Induces Alterations in Cell Morphology and Cell-Cell Interactions

CCMP-1 transfected HEK 293 cells and parental HEK 293 cells were cultured for 24 hr and followed by overnight incubation in the presence or absence of 500 ng/ml LERK8-Fc.

Untreated parental HEK 293 cells grew in loose groups of cells with cell projections growing out of the cells resulting in a 'jagged' border. Both LERK-8 treated parental cells and untreated CCMP-1 transfected cells had the same morphology. Overnight incubation of the CCMP-1 transfected HEK 293 cells, however, resulted in the retraction of cell projections and the movement of cells into tight clumps, with maximal cell-cell contact and a 'smooth' border.

A time course study of the rate of change in morphology induced by LERK8-Fc demonstrated that retraction of the cell projections could be seen as early as 20 min after the addition of LERK8, with complete retraction of the projections after 40 min. The movement of cells into clumps was initiated after 40 min of LERK8 treatment and small, smooth-bordered clumps of cells had formed after 60 min of LERK8 treatment. Over the next 5 hr these groups of cells moved together to form larger associations of cells.

EXAMPLE 7

Immunohistochemical Analysis of Tumour Tissues

A polyclonal antibody was raised against CCMP-1 using the services of Covalab, France. The antibody was raised in rabbits immunized with two specific peptides whose sequences were chosen for synthesis based on plots of hydrophobicity, antigenicity, surface probability, and low identity to other known protein family members. Peptide was synthesized using Fmoc chemistry with a cysteine residue added to the end to enable specific thiol reactive coupling of Keyhole limpet Hemocyanin prior to immunization. The CCMP-1 peptide used was: GQYSRPAEFETTSERGS (SEQ ID NO:9).

To demonstrate the specificity of the antibody raised against the above peptide, Western blotting analysis of CCMP-1 and other ephrin B receptor proteins was performed. Lysate from parental HEK 293 cells was prepared. 5 µg of lysate was spiked with 1 µg of recombinant CCMP-1, or 1 µg murine ephrin B1, B2, B3, B4 or B6, or murine ephrin A1-8 receptor proteins (R & D systems) followed by separation by 1D-SDS-PAGE. The gel was transferred to PVDF membrane and probed with the polyclonal antibody raised against the peptide described above (SEQ ID NO:9). Protein was detected using streptavidin-HRP in conjugation with a biotinylated secondary antibody. The results indicated that the antibody recognized only recombinant CCMP-1 and murine ephrin B3 receptor protein (R & D systems), but not the other ephrin B or ephrin A receptor family members.

Immunohistochemical analysis was carried out on formalin-fixed paraffin-embedded tissue microarrays containing 1 mm sections of breast carcinoma tissue from 55 donors as well as 20 sections of various normal tissues (Clinomics Laboratories Inc., 165 Tor Court, Pittsfield, Mass. 01201). Slides were deparafinised by 2×5 min washes in xylene then rehydrated through successive graded ethanol solutions and washed for 5 min in PBS. Antigen retrieval was achieved by immersing the slides in DAKO antigen retrieval solution and microwaving for 10 min at full power (950 W). In addition, detection with the antibody was improved by protease treatment of the tissue with Autozyme (AbCam) for 5 min at 37° C. The tissue was blocked in 10% donkey serum/PBS for 1 hr before addition of 1.5 µg/ml primary polyclonal antibody (in 2.5% donkey serum/PBS). Following 3 washes in PBS the tissue sections were incubated with biotin-conjugated secondary antibodies (Biotin-SP-conjugated AffiniPure Donkey anti-guinea pig, Jackson ImmunoResearch) diluted at 1:200 (2.5 µg/ml in 2.5% donkey serum/PBS) for 1 hr. Slides were washed 3 times in PBS and the tissue incubated with Streptavidin-HRP (Jackson Immunoresearch) diluted 1:100 (5 µg/ml in 2.5% donkey serum/PBS), followed by 3×5 min washes in PBS. Antibody signal was detected using DAB substrate solution (Dako Ltd.) according to the manufacturers' instructions. An adjacent tissue array was counterstained for hematoxylin and eosin (Dako Ltd.) and images were captured by a digital camera attached to a light microscope.

Results of immunohistochemical analysis of CCMP-1 on the breast tumour microarray demonstrated that CCMP-1 was present in breast carcinoma, breast adencarcinoma and breast infiltrating ductal carcinoma tissue sections. In each case, expression was generally restricted to the cancerous epithelial cells of the tumour tissue and showed a predominantly cell membrane localisation.

Results of immunohistochemical analysis of CCMP-1 on the colon cancer microarray and microarrays comprising prostate adenocarcinoma, tongue squamous cell carcinoma, larynx squamous cell carcinoma, pharynx squamous cell carcinoma, parotid carcinoma, lung squamous cell carcinoma, and a brain astrocytoma, as well as kidney carcinomas and renal cell carcinomas, bladder carcinoma and a papillary cystadenocarcinoma all showed expression of CCMP-1 predominantly localised to cancerous epithelial cells.

EXAMPLE 8

Induction of Colony Formation by CCMP-1

HEK293 cells expressing recombinant CCMP-1 in the presence and absence of 500 ng/ml LERK8-Fc, HEK 293 parental cells or HEK293 cells transfected with empty pcDNA3.1 vector (vector control cells) were assessed for colony forming ability.

6-well tissue culture plates were coated in 0.9% agar and left overnight at 37° C. in an incubator. 1,000 cells in 0.5 ml of cell media (HEK 293 pcDNA3.1 vector control cells, HEK 293 parental cells and CCMP-1 expressing HEK 293 cells) were added to 2 ml of methylcellulose-based media (ClonaCell™-TCS, StemCell Technologies Inc). This mixture was inverted 7 times and left to stand for 10 min. The 2 ml of media containing cells was then aliquoted into each well and the tissue culture plates were incubated at 37° C. 5% CO2 for 7 days. The number of colonies for each condition comprising more than one cell was scored.

| Results | |
| --- | --- |
| Cells | Number of colonies |
| HEK 293 parental | 18 |
| HEK 293 pcDNA3.1 vector control | 24 |
| CCMP-1 overexpressing HEK 293 | 157 |
| CCMP-1 overexpressing HEK 293 plus LERK8-Fc | 244 |

CCMP-1 expression in HEK 293 cells increases both the number and the size of colonies formed suggesting that CCMP-1 over-expression increases tumourigenic potential.

The invention claimed is:

1. A method of diagnosing a carcinoma in a subject, wherein the carcinoma is a colon cancer, which comprises: a) detecting and/or quantifying in a biological sample , selected from the group consisting of colon tissue, lymph node tissue, a metastasis of a colon cancer and serum obtained from said subject, a CCMP-1 polypeptide comprising the amino acid sequence of SEQ ID NO:1 to determine a level of CCMP-1 polypeptide in the biological sample,
b) comparing the level of said CCMP-1 polypeptide in the biological sample obtained from the subject with the level of CCMP-1 polypeptide in a previously determined reference range or control from a corresponding cancer free sample from a subject free from carcinoma, wherein an increase in said level of CCMP-1 polypeptide in the biological sample compared to said reference range or control is indicative of the presence of carcinoma of colon.

2. The method according to claim 1, wherein the step of detecting comprises:
   (a) contacting the sample with an antibody that specifically binds a polypeptide consisting of the amino acid sequence of SEQ ID NO:1; and
   (b) detecting whether binding has occurred between the antibody and said polypeptide in the sample.

3. The method according to claim 2, wherein step (b) comprises detecting the polypeptide using a directly or indirectly labeled detection reagent.

4. The method according to claim 2, wherein the antibody is immobilized on a solid phase.

5. The method according to claim 2, wherein the antibody is monoclonal, polyclonal, chimeric, humanized or bispecific, or is conjugated to a detectable label, second antibody or a fragment thereof.

6. A method of detecting a carcinoma in a subject, wherein the carcinoma is a colon cancer carcinoma, which comprises:
  a) detecting and/or quantifying in a colon tissue sample obtained from said subject a CCMP-1 polypeptide comprising the amino acid sequence of SEQ ID NO:1 to determine a level of CCMP-1 polypeptide in the colon tissue sample, wherein said detecting and/or quantifying comprises contacting the colon tissue sample with an antibody that specifically binds SEQ ID NO:1 and detecting whether binding has occurred between the antibody and said polypeptide in the sample; and
  b) comparing the level of said CCMP-1 polypeptide in the colon tissue sample obtained from the subject to the level of CCMP-1 polypeptide determined in normal colon tissue, wherein an increase in said level of CCMP-1 polypeptide in the colon tissue sample compared to said normal colon tissue detects carcinoma of colon.

* * * * *